United States Patent
Chen et al.

(10) Patent No.: US 11,911,353 B2
(45) Date of Patent: Feb. 27, 2024

(54) FATTY ACID SYNTHASE INHIBITOR AND APPLICATION THEREOF

(71) Applicant: Jiangnan University, Wuxi (CN)

(72) Inventors: Yongquan Chen, Wuxi (CN); Hongyan Qu, Wuxi (CN); Chunlei Tang, Wuxi (CN); Guosheng Wu, Wuxi (CN); Guozhen Cui, Wuxi (CN); Ninghan Feng, Wuxi (CN); Xiaoying Wang, Wuxi (CN); Kai Shan, Wuxi (CN); Shenglong Zhu, Wuxi (CN); Lengyun Wei, Wuxi (CN)

(73) Assignee: JIANGNAN UNIVERSITY, Wuxi (CN)

(*) Notice: Subject to any disclaimer, the term of this patent is extended or adjusted under 35 U.S.C. 154(b) by 764 days.

(21) Appl. No.: 17/085,365

(22) Filed: Oct. 30, 2020

(65) Prior Publication Data

US 2021/0046027 A1    Feb. 18, 2021

Related U.S. Application Data

(63) Continuation of application No. PCT/CN2019/096319, filed on Jul. 17, 2019.

(30) Foreign Application Priority Data

Jun. 11, 2019 (CN) .......................... 2019105003615

(51) Int. Cl.
*A61K 31/17* (2006.01)
*A61P 35/00* (2006.01)
*A61K 31/167* (2006.01)

(52) U.S. Cl.
CPC ............ *A61K 31/17* (2013.01); *A61K 31/167* (2013.01); *A61P 35/00* (2018.01)

(58) Field of Classification Search
CPC ........ A61K 31/17; A61K 31/167; A61P 35/00
USPC ........................................................ 514/563
See application file for complete search history.

(56) References Cited

U.S. PATENT DOCUMENTS

2007/0203236 A1* 8/2007 Smith et al. ......... A61K 31/202
514/560

FOREIGN PATENT DOCUMENTS

| CN | 101117328 A | 2/2008 | |
|---|---|---|---|
| CN | 105198786 A | 12/2015 | |
| EP | 2019091 A1 | 1/2009 | |
| WO | 9822432 A1 | 5/1998 | |
| WO | 9831689 A1 | 7/1998 | |
| WO | WO2008/024139 A2 * | 3/2008 | ............. A61K 31/41 |

* cited by examiner

*Primary Examiner* — Jeffrey S Lundgren
*Assistant Examiner* — Heather Raquel Dahlin
(74) *Attorney, Agent, or Firm* — IPRO, PLLC

(57) ABSTRACT

The disclosure discloses a fatty acid synthase inhibitor and application thereof and belongs to the technical field of medical biology. The fatty acid synthase inhibitor of the disclosure can significantly inhibit the activity of fatty acid synthase without affecting normal expression, and adjust the ratio of fatty acids in cells. The fatty acid synthase inhibitor of the disclosure has a good tumor proliferation inhibitory effect, can arrest the growth cycle of tumor cells in the interphase, prevent tumor cell division, inhibit tumor cell proliferation, promote tumor cell apoptosis and exert a tumor treatment effect, can be used to treat tumors and metabolism related diseases, and has an important clinical application prospect.

13 Claims, 5 Drawing Sheets

FATTY ACID SYNTHASE INHIBITOR AND APPLICATION THEREOF

TECHNICAL FIELD

The disclosure belongs to the technical field of medical biology and specifically relates to a fatty acid synthase inhibitor and application thereof.

BACKGROUND

Fatty acids in the human body include exogenous fatty acids which are directly from the outside world, and also include endogenous fatty acids synthesized in the human body. Fatty acid synthase (FASN) is a key enzyme in the synthesis process of endogenous fatty acids in organisms and catalyzes acetyl-CoA and malonyl-CoA to generate long-chain fatty acids. FASN includes 7 functional domains of acetyltransferase (AT), malonyltransferase (MT), β-ketoacyl synthase (KS), β-ketoacyl reductase (KR), β-hydroxyacyl dehydratase (HD), enoyl reductase (ER) and thioesterase (TE) and can be divided into two subtypes of a type I and a type II. FASN in bacteria and plants belongs to the type II, which is a multi-enzyme system composed of the above 7 functional domains as independent enzymes; FASN of humans and other mammals belongs to the type I, which is a single-chain multi-functional enzyme consisting of the above 7 functional domains, is encoded by a single gene and has a relative molecular mass of 250 ku. Under normal circumstances, FASN can be expressed in various tissues such as liver and fat. The function of FASN is to synthesize carbohydrates into fatty acids and store the fatty acids in the form of triglycerides. FASN also has some special functions. For example, during lactation, when co-existing with thioesterase, FASN can act to produce medium-chain fatty acids which are easy for babies to digest. Under normal physiological conditions, FASN is regulated by diets and hormones. Carbohydrate intake, thyroid, insulin and glucocorticoid can all up-regulate FASN and fatty acid synthesis, while unsaturated fatty acids, cAMP and glucagon down-regulate FASN and fatty acid synthesis.

In recent years, it has been found that FASN is closely related to obesity. FASN has relatively high expression in human liver and fat tissues, especially in liver, the fatty acid synthesis ability of FASN is 8-9 times higher than that of fat tissues, and the expression level is affected by the intake of components and hormone levels. Carbohydrate-containing diets induce the production of fat by stimulating the high expression of FASN. Therefore, the development of FASN inhibitors is expected to open up new ways for the treatment of obesity. FASN-specific small molecule inhibitors can reduce the synthesis of fatty acids by inhibiting FASN; moreover, due to hindered synthesis of fatty acids, the concentration of a substrate malonyl-CoA thereof is increased, and malonyl-CoA can directly act on the feeding center of the hypothalamus and inhibit the secretion of ingested neuropeptide Y facilitating feeding, and thus leading to the inhibition of eating. At the same time, in peripheral tissues such as liver and fat tissues, the activity of carnitine palmitoyltransferase-1 can be improved, so that oxidation of fatty acids and consumption of energy are increased, and the purpose of achieving weight loss by compensatory consumption of excess body fat is achieved. Animal experiments also show that FASN inhibitors can also relieve non-insulin-dependent diabetes, reduce the symptoms of hypertension, coronary embolism and other obesity complications and reduce the incidence rate.

Since the 1980s, researchers have successively found FASN in breast cancer, colorectal cancer, prostate cancer, ovarian cancer, endometrial cancer and other tissues, and the expression of FASN is much higher than that of normal tissues. Studies have shown that the inhibition of FASN or the reduction of the expression of FASN can effectively control the proliferation of tumor cells or induce the apoptosis of tumor cells. At present, tumor regulating mechanisms of FASN are still unclear. Some researchers believe that the inhibition of FASN to reduce the structural lipid and energy required for cell proliferation is the cause of the apoptosis of tumor cells. Some researchers have speculated that the increase of the concentration of malonyl-CoA in cells is the main reason for inhibiting FASN to cause the apoptosis of tumor cells. Other studies have shown that after FASN inhibitors are used, tumor cells arrest in a G0 phase, indicating that the synthesis of fatty acids is related to the cell cycle. The inhibition of FASN can quickly and massively inhibit tumor cell DNA replication and delay an S phase, indicating that the fatty acid synthesis pathway and the DNA synthesis activity are related to the proliferation of tumor cells.

FASN has relatively high expression in the liver and fat cells of obese patients and tumor cells of various tumor patients and has become a new drug target for the study of such diseases. The study of FASN inhibitors is of great significance for inhibiting the biosynthesis of endogenous fatty acids, thereby effectively controlling the occurrence and development of tumors, obesity and various related metabolic syndromes.

SUMMARY

In order to solve the problems above, the disclosure provides application of a compound shown as a general formula (I) or pharmaceutically acceptable salts thereof in preparation of medicines for inhibiting fatty acid synthase. The compound shown as a general formula (I) or pharmaceutically acceptable salts thereof are as follows:

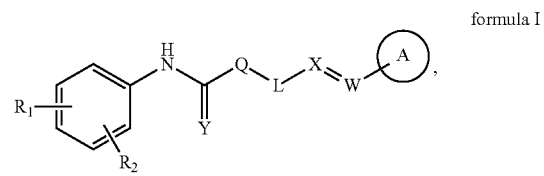

formula I wherein, ====== is a single bond or a double bond; $R_1$ and $R_2$ are each independently selected from any one of hydroxyl, halogen, $C_1$-$C_4$ alkyl and $C_1$-$C_4$ alkoxy;0 ring A is

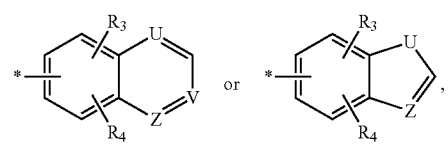

and U, V and Z are each independently selected from CH, N and NH; $R_3$ and $R_4$ are each independently selected from any one of halogen, hydroxyl, aryloxy and alkoxy; the dashed line indicates containing or not containing, that is to say, ring A contains a substituted phenyl or a substituted benzoheterocyclic group;

Q is at least one heteroatom or C$_{1-5}$ straight or branched-chain hydrocarbyl containing no heteroatoms, and the heteroatoms are independently selected from nitrogen, oxygen and sulfur;

L is keto or imino;

W is selected from any one of —(CH$_2$)$_a$, —(CH$_2$)$_a$—C(O)—, —(CH$_2$)$_a$—OC(O)— and —(CH$_2$)$_n$—C(O)O—, wherein a is a natural number of 0-3;

X is selected from —N(R)$_m$N(R)$_n$—, —C(O)N(R)$_n$— or —N(R)$_n$C(O)—, and m 10 and n are each independently 0 or 1; R is independently hydrogen, halogen or phenyl; and Y is selected from nitrogen, oxygen or sulfur.

In an embodiment of the disclosure, ring A is monocyclic aryl, naphthyl, [1,8]naphthyridinyl, benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolinyl, isoquinolinyl, oxazolo[5,4-b]pyridyl or oxazolo[5,4-c]pyridyl.

In an embodiment of the disclosure, Q is a C$_{1-5}$ straight or branched-chain hydrocarbyl with an end group of —N(R)—, —S—, —O—, —SO—, —SO$_2$—, —NRC(O)—, —C(O)NR—, —N(R)SO$_2$—, —SO$_2$N(R)—, —OC(O)— or —C(O)O—.

In an embodiment of the disclosure, Q contains at least one double bond.

In an embodiment of the disclosure, the pharmaceutically acceptable salts of the compound shown as the general formula (I) include lactate, hydrochloride, phosphate, acetate, malate, citrate or aspartate.

In an embodiment of the disclosure, the compound shown as the general formula (I) is selected from the following structures:

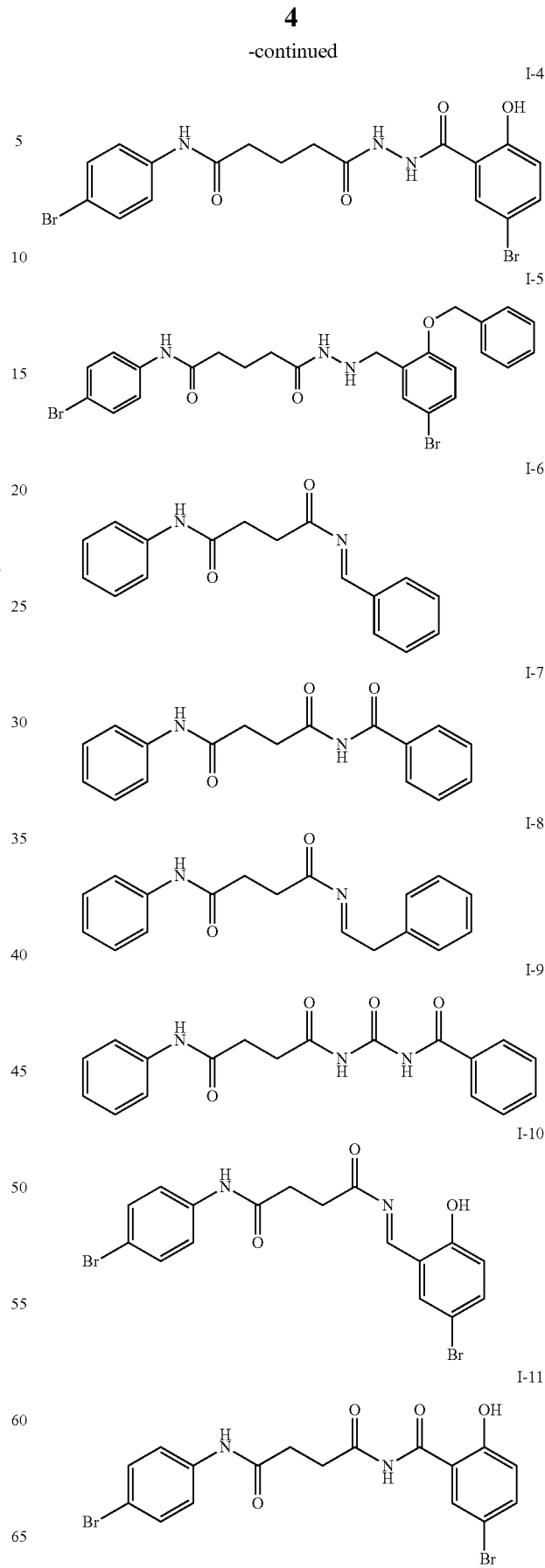

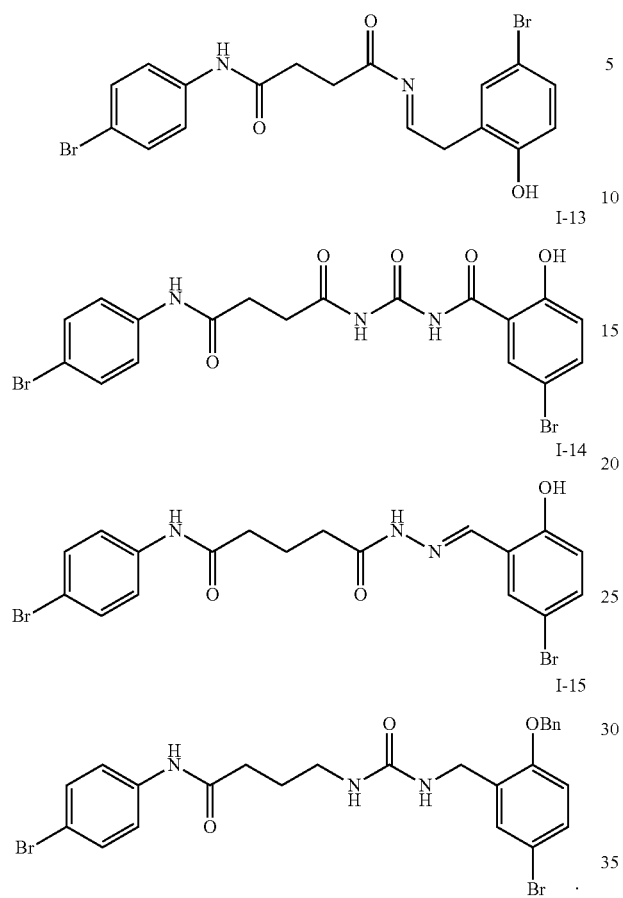

The compound shown as the general formula (I) or the pharmaceutically acceptable salts thereof provided by the disclosure can be used as a fatty acid synthase inhibitor to inhibit the activity of fatty acid synthase and play a role in regulating fatty acid compositions.

The second objective of the disclosure is to apply the compound shown as the general formula (I) or the pharmaceutically acceptable salts thereof to preparation or development of medicines for treatment of cancer, fatty acid metabolic diseases or immune diseases.

The third objective of the disclosure is to prepare or develop a medicine for treatment of fatty acid metabolic diseases, and the medicine contains the compound shown as the general formula (I) or the pharmaceutically acceptable salts thereof.

The fatty acid metabolic diseases are selected from obesity, cardio-cerebrovascular disease, hyperlipidemia, primary obesity, pulmonary hypertension, Hodgkin disease, irritable bowel syndrome, cerebrovascular accident, atherosclerosis, diabetes, glomerulonephritis and viral infection.

The fourth objective of the disclosure is to prepare or develop a medicine for treatment of cancer, and the medicine contains the compound shown as the general formula (I) or the pharmaceutically acceptable salts thereof.

The cancer is selected from ovarian cancer, breast cancer, uterine cancer, colon cancer, cervical cancer, lung cancer, prostate cancer, testicular cancer, thymic cancer, skin cancer, bladder cancer, pancreatic cancer, leukemia, lymphoma, non-small cell lung cancer, small cell lung cancer, multiple osteoma cancer, squamous cell carcinoma, kidney cancer, urethral cancer, bronchial cancer, esophageal cancer, bone cancer, throat cancer, bladder cancer, thyroid cancer, liver cancer, head and neck cancer, eye cancer, skin cancer, oral cavity, stomach cancer, colon cancer, rectal cancer, brain cancer and central nervous system cancer.

The fifth objective of the disclosure is to prepare or develop a medicine for treatment of immune diseases, and the medicine contains the compound shown as the general formula (I) or the pharmaceutically acceptable salts thereof.

The immune diseases are selected from multiple sclerosis, central nervous system injury, inflammatory bowel disease, rheumatoid arthritis, osteoarthritis, psoriasis, systemic lupus erythematosus, graft versus host disease, asthma and chronic obstructive pulmonary disease.

The dosage form of the medicines includes traditional forms, such as decoction, pills, powder, ointments, pellets, medicinal liquor, syrup, extracts, lozenges, sticks, suppositories, herbal leavens, moxa preparations and the like; the dosage form also includes modern dosage forms, such as tablets, granules, bagged steeping drugs, oral liquids, capsules, dripping pills, mixtures, tinctures, aerosols, pellicle, powder injections and injections.

The medicines also contain other medically acceptable excipients, including binders, fillers, disintegrants, lubricants, antioxidants, flavoring agents, aromatics, cosolvents, emulsifiers, solubilizers, osmotic pressure regulators and colorants.

The technical scheme provided by the disclosure has the following advantages:

(1) The compound shown as the general formula I or the pharmaceutically acceptable salts thereof in the disclosure can be used to prepare a fatty acid synthase inhibitor, which can inhibit the enzyme activity of FASN and is a new FASN inhibitor. As a major enzyme in cell lipid metabolism, FASN participates in the occurrence and development of tumors. FASN plays an important role in controlling tumor cell energy metabolism, cell cycle regulation, epithelial-mesenchymal transition and the like, and is expected to become a marker and therapeutic target for tumor diagnosis. The FASN inhibitor can effectively control the occurrence and development of cancer by inhibiting the biosynthesis of endogenous fatty acids in tumor cells. Therefore, the fatty acid synthase inhibitor of the disclosure has an obvious inhibitory effect on the enzyme activity of FASN, can arrest the growth cycle of tumor cells in the interphase, prevent tumor cell division, inhibit tumor cell proliferation, promote tumor cell apoptosis and exert a tumor treatment effect and has an important clinical application prospect.

(2) The fatty acid synthase inhibitor of the disclosure can adjust the composition and ratio of fatty acids, and can be applied to treatment of fatty acid metabolic diseases or immune system diseases.

(3) The pharmaceutical composition prepared by the fatty acid synthase inhibitor of the disclosure has a significant inhibitory effect on fatty acid enzymes, and can arrest cell cycle of tumor cells, significantly reduce transplantation tumors in the bodies of living mice and inhibit the formation of lipid droplets. Therefore, the pharmaceutical composition is an important tumor treatment prospective drug, and provides a new treatment approach for cancer or fatty acid metabolic diseases.

DETAILED DESCRIPTION

Figure 1:
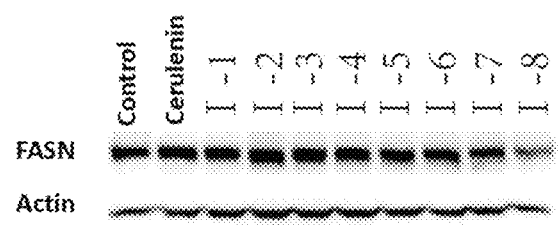
FIG. 1 shows the effect of a compound shown as a formula I on expression of FASN in prostate cancer cells PC3.

Example 1 Synthesis of Compound of Formula I-1

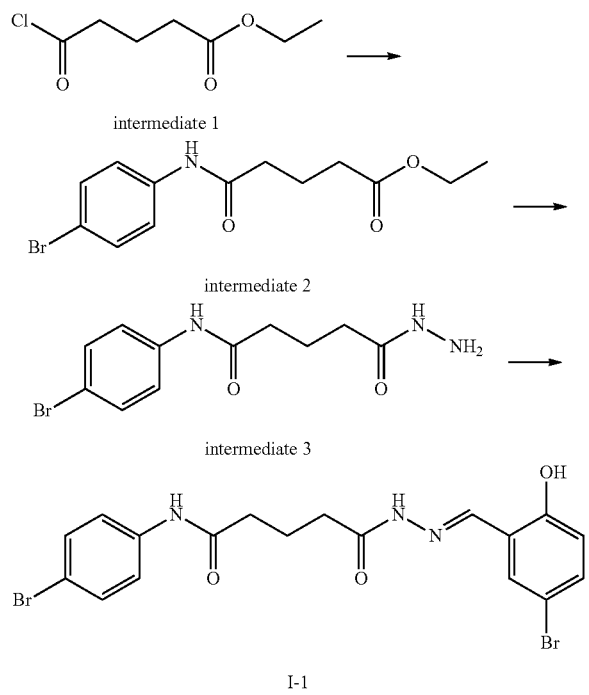

A specific synthetic method is as follows:

(1) Synthesis of an Intermediate 1 Compound 5-(4-bromophenylamino)-5-oxopentanoic acid 5-ethoxy-5-oxopentanoic acid (2 g, 12.5 mM) and dichloromethane (30 mL) are added into a 100 mL single-neck flask for ice bath cooling to 0° C., thionyl chloride (3 g, 25 mM) is slowly added, and the mixture is heated to room temperature and then heated for reflux. The reaction solution is quenched and spin-dried to obtain 1 g of intermediate 1 product with a yield of 44.9%.

(2) Synthesis of Intermediate 2 Compound Ethyl 5-(4-bromophenylamino)-5-oxopentanoate P-bromoaniline (1.15 g, 6.7 mmol), dichloromethane (15 mL) and triethylamine (0.85 g, 8.4 mmol) are added into a 100 mL single-neck flask and cooled to 0° C., the intermediate 1 (1 g, 5.6 mmol) is slowly added dropwise, the mixture is stirred overnight at room temperature, TLC shows that the reaction is completed, and the reaction solution is sequentially washed with diluted hydrochloric acid (15 mL) and a sodium bicarbonate aqueous solution (15 mL), dried with anhydrous sodium sulfate, filtered and distilled under reduced pressure to obtain 1.2 g of intermediate 2 with a yield of 68%.

(3) Synthesis of Intermediate 3 Compound N-(4-bromophenyl)-5-hydrazino-5-oxopentanamide The intermediate 2 (0.5 g, 1.6 mmol), hydrazine hydrate (80%, 0.6 g, 9.5 mmol) and ethanol (5 mL) are added into a 20 mL single-neck flask and heated to 90° C. for reflux for 2 hours. TLC shows that the reaction is completed, the solvent is evaporated under reduced pressure, and silica gel column chromatography (petroleum ether:ethyl acetate=100:1-3:1) is performed to obtain 0.4 g of intermediate 3 with a yield of 83%.

(4) Synthesis of Compound I-1

The intermediate 3 (0.4 g, 1.3 mmol), 5-bromo-2-hydroxybenzaldehyde (0.4 g, 1.95 mmol), sodium hydroxide (0.52 g, 13 mmol) and methanol (5 mL) are added into a 20 mL single-neck flask and stirred at room temperature for 3 days. The reaction solution is filtered and spin-dried to obtain a crude product, which is beaten with DMF to obtain 0.5 g of product with a yield of 80%.

$^1$H-NMR (DMSO, 400 MHz) δ: 1.85 (t, 2H), 2.27 (d, 1H), 2.35 (t, 2H), 2.64 (t, 1H), 6.83 (m, 1H), 7.40 (m, 2H)), 7.54 (m, 2H), 7.23 (d, 1H), 10.03 (d, 2H), 10.34 (s, 1H), 11.24 (d, 1H), 11.69 (s, 1H). Mass spectrum (MS+): 482, 483 m/z: [M+1, M+2].

Example 2 Synthesis of Compound of Formula I-2

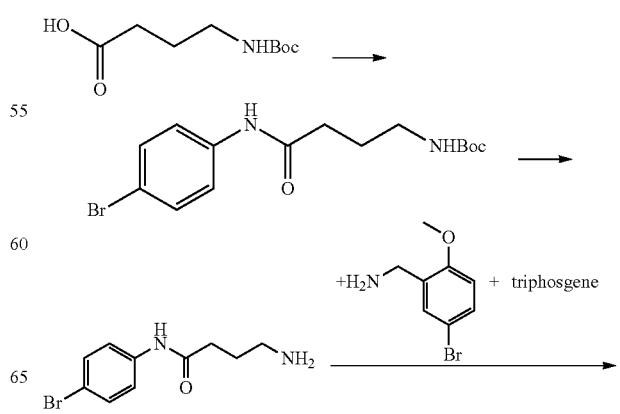

-continued

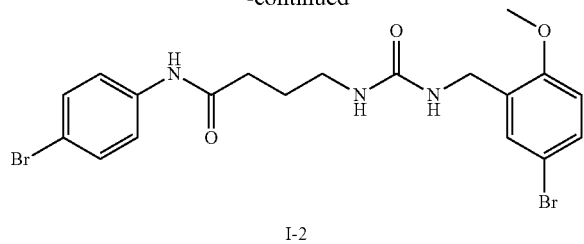

I-2

(1) Synthesis of 4-((tert-butoxycarbonyl)amino)butyric acid 4-aminobutyric acid (2 g, 19.4 mmol, 1.0 eq), THF (15 mL), water (15 mL) and sodium hydroxide (1.6 g, 38.8 mmol) are added into a 100 mL single-neck flask and cooled to 0° C., (Boc)$_2$O (5.1 g, 23.3 mmol) is slowly added dropwise, and after dropping, the mixture is stirred at 25° C. for 12 hours. After the reaction is completed, THF is discarded by rotary evaporation, 15 mL of water and ethyl acetate (10 mL) are added for extraction to remove excess (Boc)$_2$O, the pH of an aqueous phase is adjusted to 2-3 with citric acid or diluted hydrochloric acid, ethyl acetate (15 mL) is used for extraction, and an organic phase is dried with anhydrous sodium sulfate and then spin-dried to obtain 3.5 g of product with a yield of 88%.

(2) Synthesis of N-(4-bromophenyl)-4-((tert-butoxycarbonyl)amino)butyramide

P-bromoaniline (1 g, 5.8 mmol), dichloromethane (15 mL) and triethylamine (0.76 g, 7.4 mmol) are added into a 100 mL single-neck flask and cooled to 0° C., the intermediate 1 (1 g, 5.6 mmol) is slowly added dropwise, the mixture is stirred overnight at room temperature, TLC shows that the reaction is completed, and the reaction solution is sequentially washed with diluted hydrochloric acid (15 mL) and a sodium bicarbonate aqueous solution (15 mL), dried with anhydrous sodium sulfate, filtered and distilled under reduced pressure to obtain 1.2 g of product N-(4-bromophenyl)-4-((tert-butoxycarbonyl)amino)butyramide with a yield of 61%.

(3) Synthesis of 4-amino-N-(4-bromophenyl)-butyramide

The intermediate 2 (0.5 g, 1.4 mmol) and dichloromethane (5 mL) are added into a 100 mL single-neck flask and cooled to 0° C., trifluoroacetic acid (1.5 mL) is slowly added dropwise, the mixture is stirred at room temperature for 3 hours, TLC shows that the reaction is completed, the pH of the reaction solution is adjusted to 7 with saturated sodium bicarbonate, the solution is separated, and an organic phase is dried with anhydrous sodium sulfate, filtered and spin-dried to obtain 0.25 g of product 4-amino-N-(4-bromophenyl)-butyramide with a yield of 69.4%.

(4) Synthesis of Compound I-2

Triphosgene (114 mg, 0.385 mmol) is dissolved in dichloromethane (5 mL) and cooled to −10° C., a dichloromethane (3 mL) solution of 2-methoxy-5-bromobenzylamine (238 mg, 1.1 mmol) is slowly added dropwise, and after dropping, the mixture is stirred at −10° C. for 30 minutes. The temperature is then raised to 0 C, and a DCM-THF solution of 4-amino-N-(4-bromophenyl)-butanamide (280 mg, 1.1 mmol) is added. After addition, the mixture is placed at room temperature overnight. TLC shows that the reaction is completed, the pH of the reaction solution is adjusted to 7 with saturated sodium bicarbonate, the solution is separated, an organic phase is dried with anhydrous sodium sulfate, filtered and spin-dried to obtain a crude product, and the crude product is subjected to silica gel column chromatography (petroleum ether:ethyl acetate=100:1-3:1) and purification to obtain 0.2 g of I-2 with a yield of 37%.

$^1$H-NMR (DMSO, 400 MHz) δ: 1.64 (m, 2H), 2.31 (t, 2H), 3.04 (t, 2H), 3.80 (s, 3H) 4.14 (d, 2H), 6.16 (t, 1H), 6.26 (t, 1H), 6.91 (d, 1H), 7.22 (s, 1H), 7.36 (d, 1H), 7.40 (m, 2H), 7.62 (m, 2H), 10.11 (s, 1H). Mass spectrum (MS+): 499, 501, m/z: [M+2, M+4].

Example 3 Synthesis of Compound of Formula I-3

The structure of a compound I-3 is shown as follows:

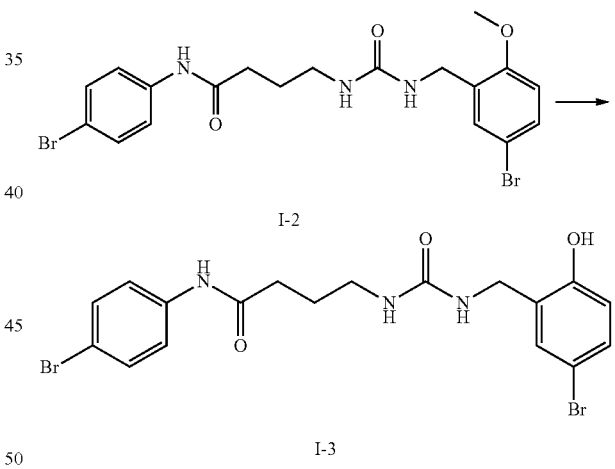

The compound I-2 (0.6 mmol) is dissolved in dichloromethane (5 mL) and cooled to −20° C., and BBr$_3$ (0.9 mmol) is slowly added. The mixture is stirred at room temperature for 3 hours. TLC shows that the reaction is completed. Water (15 mL) is added for quenching, DCM (15 mL) is used for extraction, an organic phase is dried and then dried with anhydrous sodium sulfate, filtered and spin-dried to obtain a crude product, and the crude product is subjected to silica gel column chromatography (petroleum ether:ethyl acetate=100:1-3:1) and purification to obtain 200 mg of compound I-3 with a yield of 69%.

$^1$H-NMR (DMSO, 400 MHz) δ: 1.65 (m, 2H), 2.31 (t, 2H), 3.05 (t, 2H), 4.13 (d, 2H), 6.22 (t, 1H), 6.46 (t, 1H), 6.74 (t, 1H), 7.20 (m, 2H), 7.52 (m, 2H), 7.60 (m, 2H), 10.05 (s, 1H), 10.12 (s, 1H). Mass spectrum (MS+): 485, 487, m/z: [M+2, M+4].

Example 4 Synthesis of Compound of Formula I-4

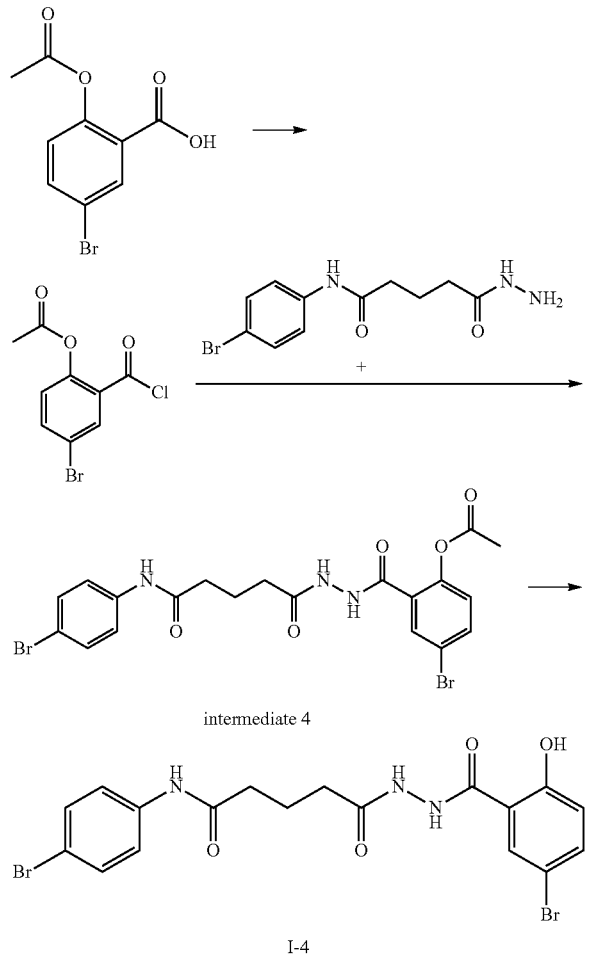

The specific synthesis includes the following steps:

(1) Synthesis of 2-formyloxy-5-bromobenzoic acid 5-bromo-2-hydroxyphenylacetic acid (4.6 mmol) and acetic anhydride (9.2 mmpl) are added into a 50 mL single-neck flask, and a drop of concentrated sulfuric acid is added dropwise. A reaction is carried out at room temperature for 3 hours. After the reaction is completed, the reaction solution is poured into ice water, and solids are separated out, filtered and dried to obtain 1 g of product 2-formyloxy-5-bromobenzoic acid with a yield of 83.3%.

(2) Synthesis of Methyl 2-chloroformylbenzene-4-bromobenzoate 2-formyloxy-5-bromobenzoic acid (3.86 mmol) and dichloromethane (10 mL) are added into a 50 mL single-neck flask and cooled to 0° C., thionyl chloride (4.64 mmol) is slowly added dropwise, the mixture is stirred for reflux for 2 hours, and after the reaction is completed, the reaction solution is spin-dried to obtain 1 g of product methyl 2-chloroformylbenzene-4-bromobenzoate with a yield of 83.3%.

(3) Synthesis of the Following Intermediate 4 Compound

The intermediate 3 compound (0.64 g, 2.12 mmol) in Example 1, tetrahydrofuran (10 mL) and triethylamine (257 mg, 2.54 mmol) are added into a 50 mL single-neck flask and cooled to 0° C., a tetrahydrofuran (6 mL) solution of methyl 2-chloroformylbenzene-4-bromobenzoate (593 mg, 1.92 mmol) is slowly added dropwise, and the mixture is stirred at room temperature overnight. After the reaction is completed, 25 mL of water is added, the pH of the reaction solution is adjusted to 4 with HCl (1 N), ethyl acetate is used for extraction, and an organic phase is discarded. The pH of an aqueous phase is adjusted to 9 with sodium carbonate, ethyl acetate (3*10 mL) is used for extraction, an organic phase is dried with anhydrous sodium sulfate, filtered and spin-dried to obtain a crude product, and the crude product is subjected to silica gel column chromatography (dichloromethane:methanol=100:1-5:1) and purification to obtain 763 mg of intermediate 4 compound with a yield of 60%.

(4) Synthesis of Compound I-4

The intermediate 4 (763 mg, 1.4 mmol), potassium carbonate (1 g, 7.2 mmol) and methanol (10 mL) are added into a 50 mL single-neck flask and stirred at room temperature overnight. After the reaction is completed, the reaction solution is filtered and blow-dried with nitrogen, 15 mL of water is added, ethyl acetate (3*10 mL) is used for extraction, an organic phase is dried with anhydrous sodium sulfate, filtered and spin-dried to obtain a crude product, and the crude product is subjected to silica gel column chromatography (dichloromethane:methanol=100:1-5:1) and purification to obtain 565 mg of compound I-4 with a yield of 80%.

$^1$H-NMR (DMSO, 400 MHz) δ: 1.81 (m, 2H), 2.25 (m, 2H), 2.44 (m, 2H), 6.85 (m, 1H), 7.48 (m, 2H), 7.53 (m, 3H), 8.01 (s, 1H), 10.05 (d, 1H), 10.32 (s, 1H), 10.5-11.8 (1H). Mass spectrum (MS+): 499, 501, m/z: [M+2, M+4].

Example 5 Synthesis of Compound of Formula I-5

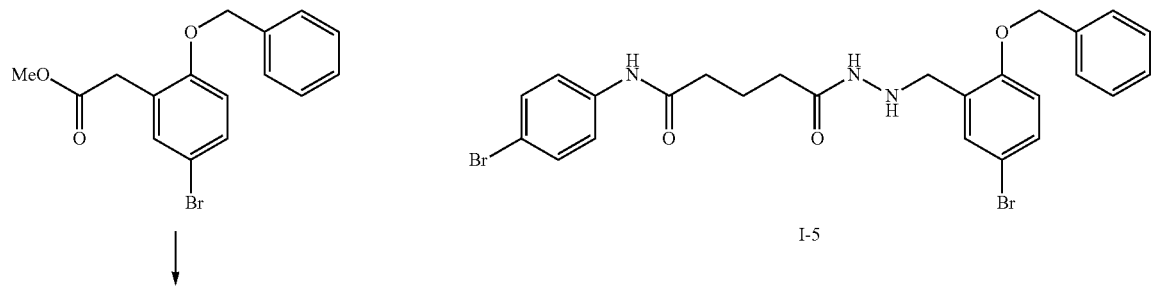

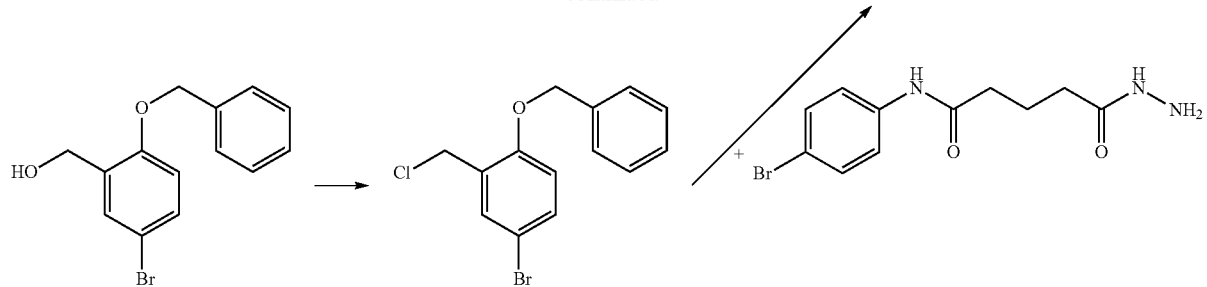

The specific synthesis includes the following steps:

(1) Synthesis of Methyl 5-bromo-2-benzyloxyphenylacetate

Methyl 5-bromo-2-hydroxyphenylacetate (1 g, 4.32 mmol), potassium carbonate (1.2 g, 8.64 mmol) and DMF (10 mL) are added into a 50 mL single-neck flask and stirred at room temperature for 10 minutes, and benzyl bromide (0.74 mg, 4.32 mmol) is added. The mixture is stirred at room temperature for 2 hours, and TLC shows that the reaction is completed. 20 mL of water is added into the reaction solution, the pH is adjusted to 4 with 1 n hydrochloric acid, ethyl acetate (2*10 mL) is used for extraction, and an organic phase is discarded. The pH of an aqueous phase is adjusted to 8 with sodium carbonate, ethyl acetate (3*10 mL) is used for extraction, and an organic phase is washed with a saturated salt solution (20 mL), dried with anhydrous sodium sulfate, filtered and spin-dried to obtain 1.1 g of product methyl 5-bromo-2-benzyloxyphenylacetate with a yield of 80%.

(2) Synthesis of 5-bromo-2-benzyloxybenzyl alcohol

The intermediate 1 (1.1 g, 3.4 mmol), THF (11 mL) and a LiOH aqueous solution (5 mL) are added into a 50 mL single-neck flask. The mixture is stirred at room temperature overnight, and TLC shows that the reaction is completed. The THF solution in the reaction solution is spin-dried, an aqueous phase is washed with ethyl acetate, the pH is adjusted to 2-3, and the mixture is filtered and dried to obtain 0.84 g of product 5-bromo-2-benzyloxybenzyl alcohol with a yield of 80%.

(3) Synthesis of 5-bromo-2-benzyloxychloromethylbenzene 5-bromo-2-benzyloxybenzyl alcohol (1 g, 3.86 mmol) and dichloromethane (10 mL) are added into a 50 mL single-neck flask and cooled to 0° C., thionyl chloride (560 mg, 4.64 mmol) is slowly added dropwise, the mixture is stirred for reflux for 2 hours, and after the reaction is completed, the reaction solution is spin-dried to obtain 0.76 g of product 5-bromo-2-benzyloxychloromethylbenzene with a yield of 85%.

(4) Synthesis of Compound I-5

The intermediate 3 compound (0.7 g, 2.58 mmol) in Example 1, tetrahydrofuran (10 mL) and triethylamine (257 mg, 2.54 mmol) are added into a 50 mL single-neck flask and cooled to 0° C., and a tetrahydrofuran (8 mL) solution of 5-bromo-2-benzyloxychloromethylbenzene (0.76 g, 2.34 mmol) is slowly added dropwise. The mixture is stirred at room temperature overnight. After the reaction is completed, 25 mL of water is added, the pH of the reaction solution is adjusted to 4 with HCl (1 n), ethyl acetate is used for extraction, and an organic phase is discarded. The pH of an aqueous phase is adjusted to 9 with sodium carbonate, ethyl acetate (3*10 mL) is used for extraction, an organic phase is dried with anhydrous sodium sulfate, filtered and spin-dried to obtain a crude product, and the crude product is subjected to silica gel column chromatography (dichloromethane:methanol=100:1-5:1) and purification to obtain 1.03 g of I-5 with a yield of 75%.

$^1$H-NMR (DMSO, 400 MHz) δ: 1.86 (m, 2H), 2.25 (m, 2H), 2.37 (m, 2H), 5.27 (s, 2H), 7.10 (m, 1H), 7.38 (m, 1H)), 7.45 (m, 2H), 7.50 (m, 4H), 7.59 (m, 2H), 7.64 (m, 1H), 7.70 (m, 1H), 10.07 (s, 2H), 10.14 (s, 1H). Mass spectrum (MS+): 589, 591, m/z: [M+2, M+4].

Example 6 Synthesis of Compound of Formula I-6

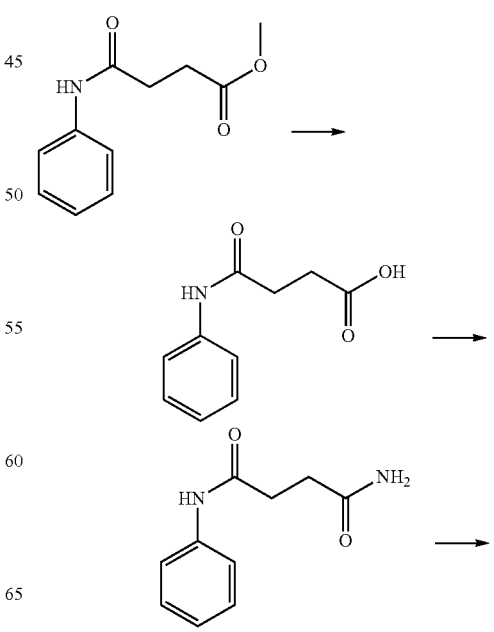

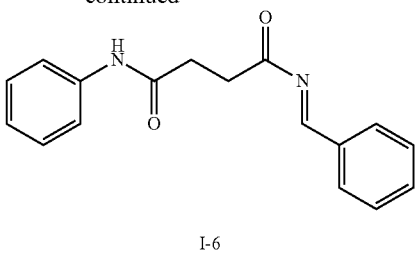

I-6

The specific synthesis includes the following steps:

(1) Synthesis of Methyl 4-carbonyl-4-(phenylamino)butyrate 5.8 mmol aniline and 8.4 mmol dihydro-3H-pyran-2,6-dione (cas No. 108-55-4) are added into a 250 ml three-neck flask for synthesis of an intermediate 5-(4-bromophenylamino)-5-oxopentanoic acid under the presence of 15 mL of organic solvent AcOH. An intermediate 1 is produced with a reaction yield of 80% at a temperature of 0-20° C.

(2) Synthesis of 4-carbonyl-4-(phenylamino)butyric acid 20 ml of methanol, methyl 4-carbonyl-4-(phenylamino) butyrate (1 g) and NaOH (0.8 g) are added into a 50 ml flask, heated at 70° C. for reflux for 5 hours and then placed at room temperature for cooling, 1 M diluted hydrochloric acid is added for adjusting the pH to 4, ethyl acetate is used for extraction, and an organic phase is separated, dried and concentrated under reduced pressure to obtain 4-carbonyl-4-(phenylamino) butyric acid.

(3) Synthesis of 4-carbonyl-4-(phenylamino)butanamide 20 ml of DMF, 4-carbonyl-4-(phenylamino)butyric acid (0.5 g), HOBT (0.3 g) and EDC (0.3 g) are added into a 50 ml flask and stirred at room temperature for 5 hours, ammonium chloride (0.25 g) is added, the mixture is stirred at room temperature for 24 hours, 20 ml of water is added, ethyl acetate is used for extraction, and an organic phase is separated, dried and concentrated under reduced pressure to obtain a 4-carbonyl-4-(phenylamino)butanamide product.

(4) Synthesis of Compound of Formula I-6

4-carbonyl-4-(phenylamino)butanamide (1.3 mmol), benzaldehyde (1.95 mmol), sodium hydroxide (0.52 g, 13 mmol) and methanol (5 mL) are added into a 20 mL single-neck flask and stirred at room temperature for 3 days. The reaction solution is filtered and spin-dried to obtain a crude product, which is beaten with DMF to obtain 0.3 g of product with a yield of 85%. The NMR hydrogen spectrum data of the obtained product are as follows:

$^1$H-NMR (DMSO, 400 MHz) δ: 2.60 (t, 2H), 2.78 (t, 2H), 7.07 (t, 1H), 7.30 (t, 2H), 7.55 (t, 2H), 7.56 (d, 2H), 7.76 (d, 2H), 9.24 (s, 1H), 9.97 (s, 1H).

Example 7 Synthesis of Compound of Formula I-7

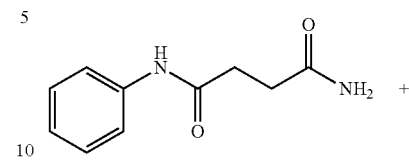

I-7

Reference is made to Example 6 for specific synthesis steps, and a compound I-7 is obtained by replacing benzaldehyde in step (4) with benzoyl chloride. The yield is 81%.

$^1$H-NMR (DMSO, 400 MHz) δ: 2.55 (t, 2H), 2.60 (t, 2H), 7.07 (t, 1H), 7.30 (t, 2H), 7.55 (t, 2H), 7.56 (d, 2H), 7.99 (d, 2H), 9.97 (s, 1H), 11.69 (s, 1H).

Example 8 Synthesis of Compound of Formula I-8

I-8

Reference is made to Example 6 for specific synthesis steps, and only benzaldehyde in step (4) is replaced with phenylacetaldehyde. The yield is 83%.

$^1$H-NMR (DMSO, 400 MHz) δ: 2.60 (t, 2H), 2.78 (t, 2H), 3.39 (s, 2H), 7.07 (t, 1H), 7.22 (t, 1H), 7.24 (d, 2H), 7.27 (t, 2H), 7.30 (t, 2H), 7.56 (d, 2H), 8.50 (t, 1H), 9.91 (s, 1H).

Example 9 Synthesis of Compound of Formula I-9

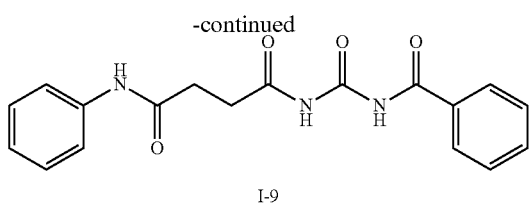

I-9

Urea, 13.5 mmol 4-carbonyl-4-(phenylamino)butyryl chloride and 1.5 g of NaOH are added into a 100 ml single-neck flask, the flask mouth is sealed, the reaction time is 1 hour, and then 6.8 mmol benzoyl chloride is added for reaction for 1 hour. 20 ml of water is added into the reaction solution, ethyl acetate is used for extraction, an organic phase is dried and evaporated to dryness under reduced pressure, and a crude product is subjected to column chromatography to obtain a final product with a yield of 83%.

$^1$H-NMR (DMSO, 400 MHz) δ: 2.55 (t, 2H), 2.60 (t, 2H), 7.07 (t, 1H), 7.30 (t, 2H), 7.55 (t, 2H), 7.56 (d, 2H), 7.99 (d, 2H), 9.97 (s, 1H), 10.91 (s, 2H).

Example 10 Synthesis of Compound of Formula I-10

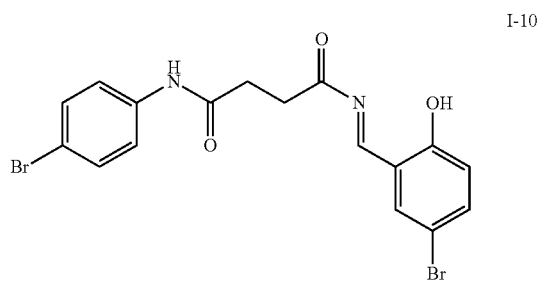 [SMILES: O=C(CCC(=O)Nc1ccc(Br)cc1)/N=C/c1cc(Br)ccc1O]

I-10

Reference is made to Example 6 for specific synthesis steps, only benzaldehyde in step (4) is replaced with 2-hydroxy-5-bromophenylacetaldehyde, and the yield is 84%.

$^1$H-NMR (DMSO, 400 MHz) δ: 2.60 (t, 2H), 2.78 (t, 2H), 6.81 (d, 1H), 7.38 (d, 1H), 7.52 (d, 4H), 7.59 (s, 1H), 9.24 (s, 1H), 9.97 (s, 1H), 12.72 (s, 1H).

Example 11 Synthesis of Compound of Formula I-11

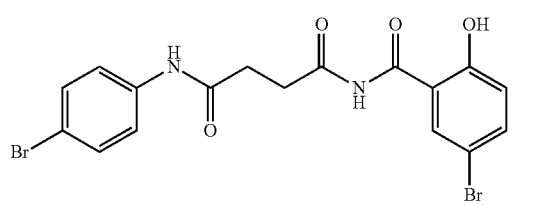

I-11

6.7 mmol 4-((4-bromophenyl)amino)-4-carbonylbutyryl chloride, 8.4 mmol 5-bromo-2-hydroxybenzamide and 0.85 g of triethylamine are added into a 100 ml single-neck flask, 20 ml of water is added into the reaction solution, ethyl acetate is used for extraction, an organic phase is dried and evaporated to dryness under reduced pressure, and a crude product is subjected to column chromatography to obtain a final product compound of a formula I-11 with a yield of 83%.

$^1$H-NMR (DMSO, 400 MHz) δ: 2.55 (t, 2H), 2.60 (t, 2H), 6.88 (d, 1H), 7.52 (d, 4H), 7.66 (d, 1H), 8.00 (s, 2H), 9.97 (s, 1H), 11.11 (s, 1H), 11.69 (s, 1H).

Example 12 Synthesis of Compound of Formula I-12

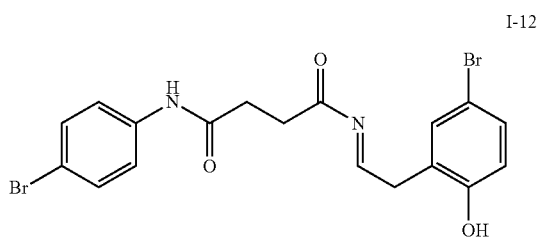 [SMILES: O=C(CCC(=O)Nc1ccc(Br)cc1)/N=C/Cc1cc(Br)ccc1O]

I-12

2.2 mmol N-(4-bromophenyl)-5-hydrazino-5-oxopentanamide, 13 mmol 5-bromo-2-hydroxyphenylacetaldehyde and 1.5 g of NaOH are added into a 100 ml single-neck flask, the flask mouth is sealed, the reaction time is 3 days, and a product is filtered and evaporated to dryness under reduced pressure to obtain a final product with a yield of 83%.

$^1$H-NMR (DMSO, 400 MHz) δ: 2.60 (t, 2H), 2.78 (t, 2H), 3.39 (d, 2H), 7.25 (d, 1H), 7.43 (s, 1H), 7.52 (d, 4H), 8.50 (t, 1H), 9.68 (s, 1H), 9.97 (s, 1H).

Example 13 Synthesis of Compound of Formula I-13

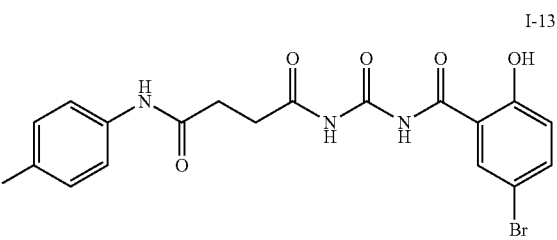

I-13

The synthesis steps of a compound I-13 are the same as those of the compound I-9, except that benzoyl chloride is replaced with 2-hydroxy-5-bromobenzoyl chloride to obtain the compound I-13 with a yield of 81%.

$^1$H-NMR (DMSO, 400 MHz) δ: 2.55 (t, 2H), 2.60 (t, 2H), 6.88 (d, 1H), 7.52 (d, 4H), 7.66 (d, 1H), 8.00 (s, 1H), 8.92 (d, 2H), 9.97 (s, 1H), 10.91 (s, 1H), 11.11 (s, 1H), 11.77 (s, 1H).

Example 14 Synthesis of Compound of Formula I-14

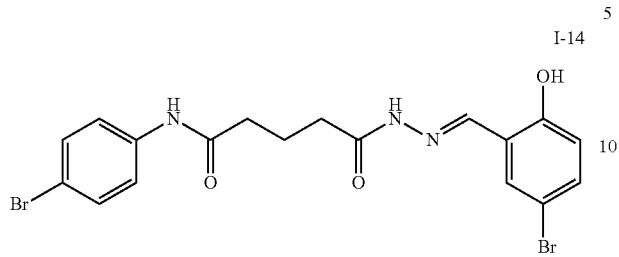

I-14

1.9 mmol N-(4-bromophenyl)-5-hydrazino-5-oxopentanamide, 4.32 mmol 5-bromo-2-hydroxybenzaldehyde and 3 g of NaOH are added into a 100 ml single-neck flask, the flask mouth is sealed, the reaction time is 3 days, a product is filtered and evaporated to dryness under reduced pressure to obtain a final product with a yield of 73%.

$^1$H-NMR (DMSO, 400 MHz) δ: 2.13 (m, 2H), 2.34 (t, 2H), 2.39 (t, 2H), 6.90 (d, 1H), 7.38 (d, 1H), 7.52 (d, 4H)), 7.80 (s, 1H), 8.78 (s, 1H), 10.05 (s, 1H), 11.07 (s, 1H), 11.19 (s, 1H).

Example 15

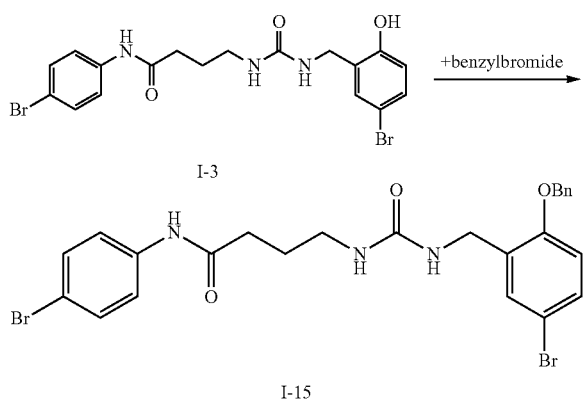

1 mmol compound I-3 and 1.92 mmol triethylamine are added into a 100 ml single-neck flask, 2.16 mmol benzyl bromide is added under an ice bath, the mixture is stirred at room temperature for 2 hours, and a product is filtered and evaporated to dryness under reduced pressure to obtain a final product with a yield of 85%.

$^1$H-NMR (DMSO, 400 MHz) δ: 2.01 (m, 2H), 2.44 (t, 2H), 3.38 (t, 2H), 4.43 (d, 2H), 5.18 (m, 2H), 6.02 (s, 2H), 6.86 (m, 1H), 7.19 (m, 1H), 7.35 (m, 4H), 7.48 (m, 2H), 7.56 (m, 2H), 7.87 (m, 1H), 7.70 (m, 2H).

Example 16

The effect of a compound shown as the following formula I-1 on the activity of FASN in colon cancer cells HCT116 is detected:

FASN Enzyme Activity Detection:

(1) Cells in the logarithmic phase are collected, the concentration of a cell suspension is adjusted, and it is appropriate to place $2*10^6$ cells in each culture dish with a diameter of 6 cm.

(2) The cells are incubated under 5% CO2 at 37° C., an original culture medium is discarded after complete cell adherence, 6 ml of 1% FBS culture medium containing 20 µM of compound I-1 is added into the cells in each dish, and 6 ml of 1% FBS culture medium containing 20 µM cerulenin is added and used as a positive control.

(3) After 4 hours of incubation, the supernatant is discarded, trypsinization is performed for 2 minutes, a complete culture medium 2 to 4 times the trypsin volume is used for stopping the digestion, the cells are centrifuged at 1000 rpm for 5 minutes, the supernatant is discarded, the cells are resuspended in 5 ml of DPBS, 500 µl to 1.5 ml of the cells are placed into an EP tube for protein quantification, the rest is centrifuged, and the supernatant is discarded fully.

(4) The cells are resuspended in 1 ml of 10 mM KH2PO4/KOH buffer (containing 4 mM DTT, 0.3 mg/ml BSA, 2.5 Mm EDTA) with the pH of 6.5, NADPH, acetyl-CoA and malonyl-CoA are added to make the final concentration reach 0.14 mM, 0.18 mM and 0.09 mM respectively, the absorbance value is measured at 340 nm, and the measurement time is 1 minute.

Definition of FASN enzyme activity: definition of activity unit: 1 µmol NADPH oxidized per milligram of protein per minute at 37° C. is 1 U;

$$FASN(U/mg\ protein) = [(\Delta A_{measuring\ tube} - \Delta A_{blank\ tube})] \div \varepsilon \div d * V_{total} * 106] \div (CPr * V_{sample}) \div T = 1.16 * (\Delta A_{measuring\ tube} - \Delta A_{blank\ tube}) \div Cpr;$$

The effect(inhibition rate) of an inhibitor on FASN enzyme activity is defined as:FASN (%)=[1−(FASN$_{inhibitor}$÷FASN$_{control}$)]*100%;

wherein ε: NADPH molar extinction coefficient, $6.22*10^3$ l/mol/cm; d: cuvette optical path, 1 cm; $V_{total}$: total volume of a reaction system, 1000 µL=0.001 L; Cpr: supernatant protein concentration, mg/ml; $V_{sample}$: the volume of a supernatant added into the reaction system, 100 µl=0.1 ml; T: reaction time, 1 min; FASN$_{inhibitor}$: FASN enzyme activity of cells treated with various inhibitors; FASN$_{control}$: FASN enzyme activity of cells without inhibitor treatment.

IC50 Value Measurement:

IC50 (half maximal inhibitory concentration) refers to the half inhibitory concentration of a measured antagonist. It can indicate that a certain concentration of a certain drug or substance (inhibitor) induces tumor cell apoptosis by 50%, and this concentration is referred to as 50% inhibitory concentration, namely, the corresponding concentration when the ratio of apoptotic cells to the total number of cells is equal to 50%. The IC50 value can be used to measure the ability of a drug to induce apoptosis, that is, the higher the inducing ability, the lower the value, which also can indicate the tolerance degree of a certain cell to a drug on the contrary.

(1) Cells in the logarithmic phase are collected, the concentration of a cell suspension is adjusted, it is appropriate to place 100 µl cells in each well of a 96-well plate, the cells are inoculated into the plate to adjust the density of to-be-detected cells to be 1000-10000 cells/well, and edge wells are filled with sterile PBS.

(2) The cells are incubated under 5% $CO_2$ at 37° C., an original culture medium is discarded after complete cell adherence, 200 µl of 1 wt % FBS culture medium containing 0.01 µM, 0.1 µM, 1 µM, 5 µM and 10 µM compound I-1 or cerulenin is added into each well, and there are 6 wells run in duplicate. An equal volume of DMSO is added as a negative control.

(3) After 72 hours of incubation, the cells are photographed for state recording, an original culture medium is discarded, and 100 μl of serum-free culture medium containing 0.5 mg/ml MTT (3-(4,5-dimethylthiazole-2)-2,5-diphenyltetrazolium bromide, trade name thiazolyl blue) is added into each well.

(4) After 2-4 hours of incubation, an original culture medium is discarded, and 150 μl of dimethyl sulfoxide (DMSO) is added into each well and shaken at 300 rpm for 10 minutes to fully dissolve purple crystals.

(5) The absorbance of each well at $OD_{570\ nm}$ is measured by an enzyme-linked immunodetection instrument, the absorbance at OD630 nm is used as a reference, dual-wavelength measurement is carried out, and survival rate results are calculated according to the following formula:

Cell survival rate=$(OD_{570}-OD_{630})/(OD_{570\ negative\ control}-OD_{630\ negative\ control})$;

wherein, $OD_{570}$: $OD_{570}$ value of each treatment group; $OD_{630}$: $OD_{630}$ value of each treatment group; $OD_{570}$ control: $OD_{570}$ value of the negative control group; $OD_{630}$ control: $OD_{630}$ value of the negative control group.

(6) The survival rate results are processed with graphpad 6.0 software according to the concentration gradient, the analysis mode is log (inhibitor) vs. Nonlinear regression (curve fit), and the calculated IC50 value is expressed as x+/−SD.

FASN Expression Detection:

Western-blot is used for detecting the expression change of FASN protein in colon cancer cells HCT116 treated with the compound I-1 above, and the expression change of protein in colon cancer cells treated with cerulenin is used as a positive control. The specific steps of Western-blot are as follows:

A. Preparation of solutions:
(1) A 10% (w/v) sodium dodecyl sulfate (SDS) solution: 0.1 g of SDS and 1 mL of $H_2O$ deionized water are used for preparation, and the solution is stored at room temperature.
(2) A separation gel buffer: 18.15 g of Tris is weighed and dissolved in 80 ml of water, the pH is adjusted to 8.8 with HCl, and the solution is diluted with water to a final volume of 100 mL to obtain a 1.5 mmol/L Tris-HCl (pH 8.8) solution.
(3) A spacer gel buffer: 6.05 g of Tris is dissolved in 80 mL of water, the pH is adjusted to 6.8 with HCl, and the solution is diluted with water to a final volume of 100 ml to obtain a 0.5 mmol/L Tris-HCl (pH 6.8) solution.
(4) An SDS-PAGE loading buffer: 8 mL of 0.5 mol/L Tris buffer with the pH of 6.8, 6.4 mL of glycerol, 12.8 mL of 10 wt % SDS, 3.2 mL of mercaptoethanol, 1.6 mL of 0.05 wt % bromophenol blue and 32 mL of $H_2O$ are uniformly mixed for use.
(5) A Tris-glycine electrophoresis buffer: 30.3 g of Tris, 188 g of glycine and 10 g of SDS are weighed, dissolved in distilled water to 1000 mL and diluted 10 times before use.
(6) A transfer buffer: 14.4 g of glycine and 6.04 g of Tris are weighed, 200 ml of methanol is added, and finally water is added to make the total volume reach 1 l.
(7) A Tris buffer salt solution (TBS): The solution contains 20 mM Tris-HCl (pH 7.5) and 500 mM NaCl.

B. Cancer cells are washed 3 times with PBS, a lysate is added, the solution is boiled directly for 5 minutes, cooled on ice and centrifuged at 12000 rpm for 2 minutes, and the supernatant is taken and stored at −20° C. for use.

C. Measurement of protein concentration by BCA method.

A 0.5 mg/ml standard protein gradient is added into the well plate, and PBS is added to reach 20 μl; an appropriate volume (3 μl) of protein sample is added into the well plate, and PBS is added to reach 20 μl; 200 μl of BCA working solution is added into each well (prepared immediately before use) and incubated at 37° C. for 30 minutes; the absorbance at 562 nm is measured, and the protein concentration is calculated according to a standard curve and a sample volume.

D. SDS-PAGE gel electrophoresis
(1) Two cleaned glass plates are aligned and put into a clamp for clamping, and then vertically clamped on a shelf for glue pouring.
(2) Pouring of 10 wt % separation gel: TEMED (tetramethylethylenediamine) is added into the separation gel buffer and uniformly shaken immediately, the solution is poured into a gap between the two glass plates and then sealed with ethanol, and after the gel is fully solidified, the upper layer ethanol can be poured out and dried with absorbent paper.
(3) Pouring of 5 wt % spacer gel: TEMED (tetramethylethylenediamine) is added into the spacer gel buffer and uniformly shaken immediately, the solution is poured into the upper layer of the separation gel, the remaining space is filled with the spacer gel, and then a comb is inserted into the spacer gel. After the spacer gel is solidified, the comb is pulled straight up and gently pulled out.
(4) The glass plates after complement of glue pouring are placed into an electrophoresis tank, and sample loading is carried out after enough electrophoresis solution is added. After the protein content of a protein sample is measured, a 5*SDS sample loading buffer is added and boiled in boiling water for 3 minutes for uniform mixing, then sample loading is carried out, and the total protein of sample loading is 35 μg.
(5) Electrophoresis is carried out at constant pressure of 80 V to run the gel, when the sample enters the lower layer gel, electrophoresis is carried out at constant pressure of 120 V until bromophenol blue reaches the bottom of the gel, and then membrane transfer is carried out.

E. Membrane transfer
(1) Glue cutting: The glass plates are pried off, the spacer glue is scraped off after the small glass plates are removed, and glue cutting is carried out according to the molecular weight of protein and experimental needs with Marker as the control.
(2) Membrane preparation: A PVDF membrane and filter paper are cut, and the cut PVDF is placed in a 80% methanol solution for activation for 30 seconds.
(3) Membrane loading: A clamp used in membrane transfer is released to keep a black side (negative electrode) level. A sponge pad is placed on the back side, the transfer buffer is added to soak the sponge pad, the soaked filter paper is placed on the pad, and then the gel, a nitrocellulose membrane, the filter paper and the sponge pad are sequentially stacked in order. Finally, a white plate (positive electrode) is placed and loaded into a membrane transfer tank.
(4) Membrane transfer: The clamp is placed into the membrane transfer tank to make the black side of the clamp face the black side of the tank and make the white side of the clamp face the red side of the tank. Membrane transfer is carried out at 4° C. and constant current of 400 mA.

(5) The membrane is removed after membrane transfer, and a corner is marked.

F. Immune response (1) Sealing: The membrane is rinsed 3 times in TBST for 5 minutes each time. After rinsing, the nitrocellulose membrane is placed in 5% skimmed milk powder and shaken for 1 hour at room temperature.

(2) Addition of a primary antibody (FASN): The sealed nitrocellulose membrane is placed on a shaker in a washing tank containing TBST and rinsed 3 times for 5 minutes each time. The membrane is placed into a plate with the addition of the primary antibody and incubated overnight at 4° C.

(3) Addition of a secondary antibody (mouse antibody or rabbit antibody): The primary antibody is recovered, the nitrocellulose membrane is shaken and rinsed 3 times in the TBST washing tank at room temperature for 5 minutes each time, and then the rinsed nitrocellulose membrane is placed into a plate with the addition of the secondary antibody and incubated in the dark at room temperature for 45 minutes. After incubation, the nitrocellulose membrane is washed 3 times in the TBST washing tank for 5 minutes each time.

G. Chemiluminescence

Color reagents are mixed in a small centrifuge tube according to instructions of a luminescence kit and then added onto the nitrocellulose membrane, and a chemiluminescence imager is used for color developing.

Table 1 shows the effect results of the compounds I-1 to I-8 and two intermediate products on the activity of fatty acid synthase (FASN) in colon cancer cells HCT116. Compared with the control group, a variety of compounds and cerulenin can all reduce the activity of FASN in colon cancer cells. Compared with cerulenin, the inhibitory effect of the compounds I-1 to I-8 is significantly higher than that of cerulenin.

FIG. 1 shows the effects of the compounds I-1 to I-8 on the expression change of FASN in colon cancer cells HCT116. Results show that the expression of FASN is not changed significantly by adding the compounds I-1 to I-8 or cerulenin, indicating that the compounds I-1 to I-8 can inhibit the enzyme activity of FASN, but not affect the normal expression of FASN.

The results above indicate that the compounds shown as the formulas I-1 to I-8 can be used as a new type of fatty acid synthase inhibitors, forming effective inhibition of FASN. It is suggested that the compound shown as the formula I-1 can be used as a therapeutic drug for tumors, obesity and other related metabolic diseases to prevent and/or treat the occurrence and development of diseases.

Example 17

The effect of the compound shown as the formula I-1 on the proliferation of tumor cells (22RV1, PC-3, HT-29, Hela, Hep G2 and CaCo-2) is detected:

(1) Cells in the logarithmic phase are collected, the concentration of a cell suspension is adjusted, it is appropriate to place 100 µl cells in each well of a 96-well plate, the cells are inoculated into the plate to adjust the density of to-be-detected cells to be 1000-10000 cells/well, and edge wells are filled with sterile PBS.

(2) The cells are incubated under 5% CO2 at 37° C., an original culture medium is discarded after complete cell adherence, 200 µl of 1 wt % FBS culture medium containing 10 µM compound I-1 is added into each well, and there are 6 wells run in duplicate. The fatty acid synthase inhibitors C75, cerulenin and GSK2194069 (hereinafter referred to as GSK) of the same concentration are added as positive controls, and an equal volume of DMSO is added as a negative control.

(3) After 72 hours of incubation, the cells are photographed for state recording, an original culture medium is discarded, and 100 µl of serum-free culture medium containing 0.5 mg/ml MTT (3-(4,5-dimethylthiazole-2)-2,5-diphenyltetrazolium bromide, trade name thiazolyl blue) is added into each well.

(4) After 2-4 hours of incubation, an original culture medium is discarded, and 150 µl of dimethyl sulfoxide (DMSO) is added into each well and shaken at 300 rpm for 10 minutes to fully dissolve purple crystals.

(5) The absorbance of each well at $OD_{570\,nm}$ is measured by an enzyme-linked immunodetection instrument, the absorbance at $OD_{630\,nm}$ is used as a reference, dual-wavelength measurement is carried out, and results are calculated according to the following formula:

$$\text{Cell survival rate} = (OD_{570} - OD_{630}) / (OD_{570\,negative\,control} - OD_{630\,negative\,control});$$

wherein, $OD_{570}$: $OD_{570}$ value of each treatment group; $OD_{630}$: $OD_{630}$ value of each treatment group; $OD_{570}$ control: $OD_{570}$ value of the negative control group; $OD_{630}$ control: $OD_{630}$ value of the negative control group.

Figure 2:
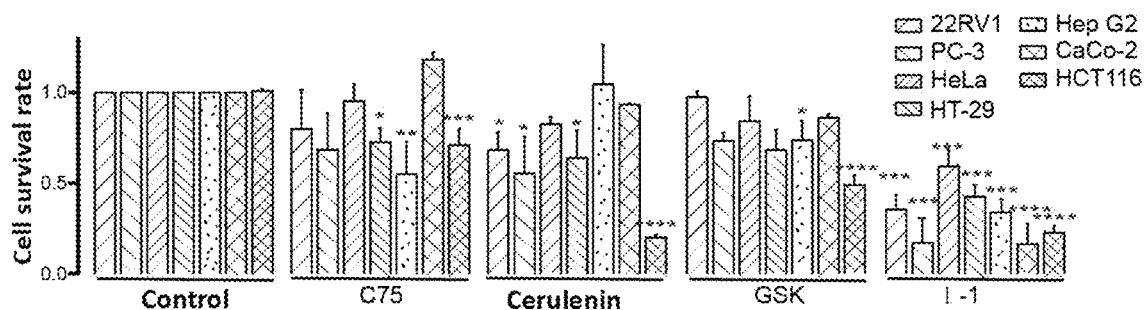
FIG. 2 shows the effect of a compound shown as a formula I on proliferation of various tumor cells.

FIG. 2 shows the effects of the fatty acid synthase inhibitors C75, cerulenin and GSK and the compound I-1 on the proliferation of 7 different tumor cells 22RV1, PC-3, HT-29, Hela, Hep G2, CaCo-2 and HCT116. It can be seen from FIG. 2 that although C75, cerulenin and GSK as fatty acid synthase inhibitors have the effects of inhibiting the proliferation of tumor cells, they have quite different effects on different types of tumor cells and have no significant effect on the proliferation of some tumor cells, and the stability is low. Compared with the three inhibitors above, the compound I-1 has a significantly improved inhibitory effect on tumor proliferation, and can effectively inhibit a variety of different types of tumor cells.

Example 18

The effect of the compound shown as the formula I-1 on the growth cycle of prostate cancer cells PC-3 is detected:

(1) The cancer cells in the logarithmic growth phase are taken and inoculated into a 6 cm culture dish with the inoculation amount of $2*10^6$ cells in each dish, and incubated under 5% CO2 at 37° C.

(2) After complete cell adherence, the cells are starved without serum for 12 hours, and 6 ml of 2% FBS culture medium containing the structural compound shown as the formula I with different concentration gradients (4 µM, 8 µM and 10 µM) is added.

(3) After 24 hours of incubation, the supernatant is discarded, trypsinization is performed for 2 minutes, a complete culture medium 2 to 4 times the trypsin volume is used for stopping the digestion, the cells are centrifuged at 1000 rpm for 5 minutes, the supernatant is discarded, the cells are washed twice in 1 ml of DPBS, and the supernatant is discarded.

(4) The cells are resuspended in 1 ml of 70% ethanol solution and stored at 4° C. for 18 hours or above to fix the cells.
(5) The cells are centrifuged, the supernatant is discarded, and the cells are washed twice with DPBS to remove residual ethanol.
(6) The cells are centrifuged, the supernatant is discarded, and the cells are incubated in 1 ml of PI staining solution in the dark at room temperature for 15 minutes and tested on a flow cytometer within 1 hour.

Figure 3:
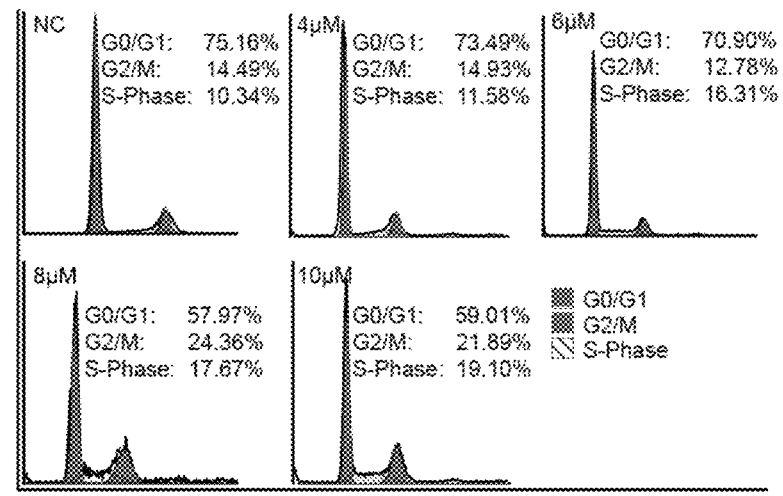
FIG. 3 shows the effect of a compound shown as a formula I on growth cycle of prostate cancer cells PC3.

FIG. 3 shows the effects of different concentrations of the structural compound shown as the formula I on the growth cycle of prostate cancer cells PC-3. FIG. 3 shows a statistical result diagram of the proportional relationship between prostate cancer cells PC-3 of the control group without inhibitor treatment and the prostate cancer cells PC-3 treated with 4 μM, 6 μM, 8 μM and 10 μM compound I-1 respectively in a G0/G1 stage, an S-Phase and a G2/M phase. It can be seen from FIG. 3 that the proportion of the PC3 cells treated with the structural compound shown as the formula I in an S phase is increased significantly from 10.34% in the control group to 19.10% in the 10 μM treatment group, thus the proportion of the tumor cells entering the division phase (M phase) and the G0/G1 phase is decreased, the inhibition of the mitosis of the prostate cancer cells PC3 shows S phase cycle arrest, and with the increase of drug concentration, the arrest condition becomes worse significantly.

Therefore, the structural compound shown as the formula I can cause an obvious S-phase cycle of PC-3, inhibit tumor cell proliferation and promote tumor cell apoptosis, and the arrest of the compound to the growth cycle of the tumor cells is concentration-dependent. It is suggested that the structural compound shown as the formula I can inhibit the occurrence and development of tumors, and is used as a new type of therapeutic drug for clinical treatment of tumors.

Example 19

The effect of the compound shown as the formula I-1 on the division of prostate cancer cells PC3 is detected:
(1) Cancer cells in the logarithmic growth phase are taken, a culture medium is discarded, trypsinization is performed for 2 minutes, a complete culture medium 2 to 4 times the trypsin volume is used for stopping the digestion, the cells are centrifuged at 1000 rpm for 5 minutes, and the supernatant is discarded.
(2) The cells are washed once in 1 ml of serum-free culture medium and centrifuged, and the supernatant is discarded.
(3) The cells are resuspended in 4 ml of serum-free culture medium and counted.
(4) The cells are added into 10 μm of CFSE working solution at 1:1 (v:v) and incubated in the dark at 37° C. for 15 minutes.
(5) Serum is added to make the final concentration reach 40%, and the cells are incubated on ice for 10 minutes to stop staining.
(6) The cells are centrifuged to remove the supernatant, resuspended in a complete culture medium, inoculated into a 6 cm culture dish with the inoculation amount of $2*10^6$ cells in each dish and incubated under 5% CO2 at 37° C.
(7) After complete cell adherence, 6 ml of 2% FBS culture medium containing 10 μM of the structural compound shown as the formula I is added.
(8) After 24 hours of incubation, the culture medium is discarded, trypsinization is performed for 2 minutes, a complete culture medium 2 to 4 times the trypsin volume is used for stopping the digestion, the cells are centrifuged at 1000 rpm for 5 minutes, the supernatant is discarded, and the cells are resuspended in 1 ml of DPBS and detected on a flow cytometer.

Figure 4:
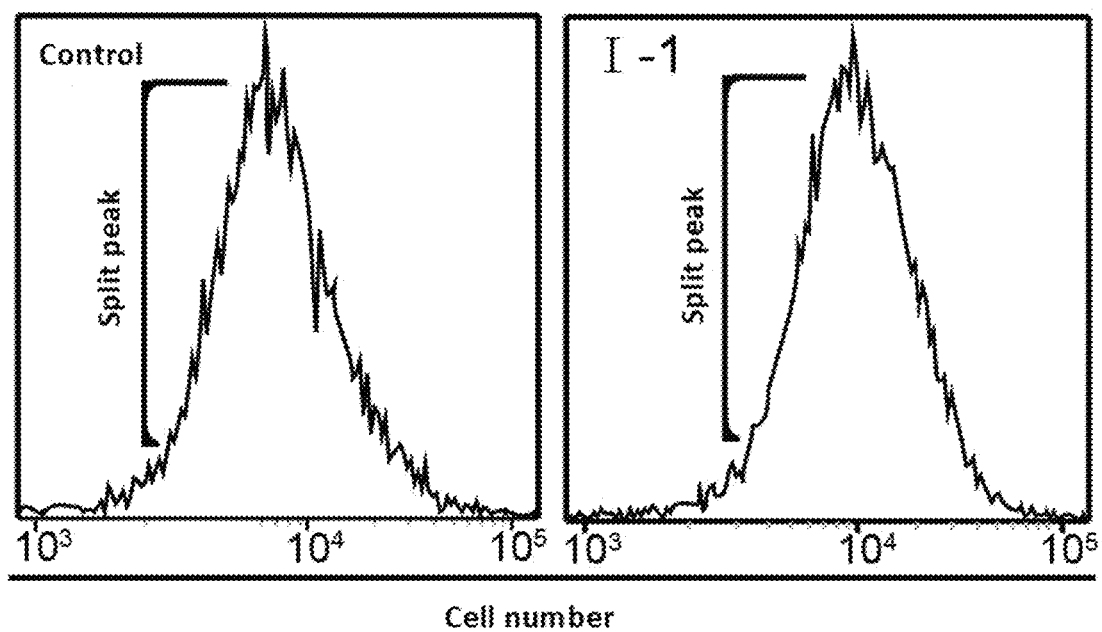
FIG. 4 shows the effect of a compound shown as a formula I on division of prostate cancer cells PC3.

FIG. 4 shows the effect of the compound shown as the formula I on the cell division of the prostate cancer cells PC-3. It can be seen from the Figure that compared with cells without addition of the compound I-1, the split peak number of the prostate cancer cells PC3 treated with the compound shown as the formula I is significantly reduced, indicating that the compound can effectively inhibit cell division and reduce the cell division number, thereby affecting the growth of cancer cells and inhibiting the tumor proliferation. It is suggested that the structural compound shown as the formula I-1 can inhibit the occurrence and development of tumors, and is used as a new type of therapeutic drug for clinical treatment of tumors.

Example 20

The effect of the structural compound shown as the formula I-1 on the content and compositions of fatty acids synthesized of tumor cells (prostate cancer cells PC-3 and colon cancer cells HCT116) is detected:
(1) The cancer cells in the logarithmic growth phase are taken and inoculated into a 6 cm culture dish with the inoculation density of $2*10^6$ cells, and incubated under 5% CO2 at 37° C.
(2) After cell adherence, 6 ml of 1% FBS culture medium containing 20 μM of the compound shown as the formula I is added into each dish with the culture medium as a negative control and cerulenin as a positive control.
(3) After 24 hours of incubation, the culture medium is discarded, trypsinization is performed for 2 minutes, a complete culture medium 2 to 4 times the trypsin volume is used for stopping the digestion, the cells are centrifuged at 1000 rpm for 5 minutes, and the supernatant is discarded.
(4) The cells are resuspended in 10 ml of DPBS, 1 ml of cell suspension is added into 1.5 ml of an ep tube for protein quantification, the remaining 9 ml of the cell suspension is centrifuged again to remove the supernatant, and an appropriate volume of internal standard is added for freeze-drying.
(5) 1 ml of 0.5 M NaOH-methanol solution is added, filled with nitrogen, subjected to vortex shaking for 30 seconds and solid bath at 100° C. for 5 minutes and cooled to room temperature.
(6) 1 ml of 40% boron trifluoride-methanol solution is added, filled with nitrogen, subjected to vortex shaking for 30 seconds and solid bath at 100° C. for 5 minutes and cooled to room temperature.
(7) 4 ml of n-hexane and 2 ml of saturated sodium chloride solution are added for vortex shaking and centrifuged at 2000 rpm for 10 minutes, the supernatant is taken and subjected to nitrogen blowing to complete dryness, and the cells are resuspended in 500 μl of n-hexane, transferred into a sample bottle and detected on a GC/MS detector.

Figure 5:
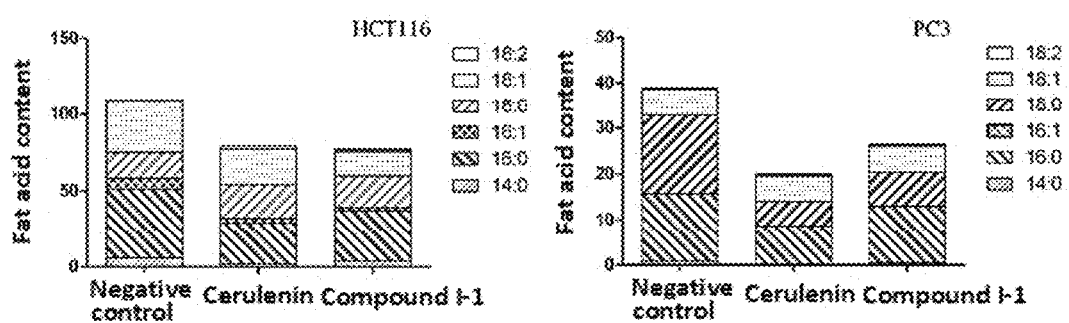
FIG. 5 shows the effect of a compound shown as a formula I on fatty acid compositions of various cancer cells.

FIG. 5 shows the effect of the compound shown as the formula I on the content and compositions of fatty acids of prostate cancer cells PC-3 and colon cancer cells HCT116, and the types of fatty acids include 18:2, 18:1, 18:0, 16:1, 16:0 and 14:0. It can be seen from FIG. 5 that the total fatty acid content of PC-3 and HCT116 cells treated with the compound shown as the formula I is significantly lower than that of the control group, and the fatty acid content of 16:0 is also lower than that of the control group, indicating that the compound shown as the formula I can inhibit the synthesis of fatty acids in PC-3 and HCT116 and change the distribution of fatty acids in tumor cells, thereby affecting tumor cell metabolism. Inhibition of fatty acid synthesis to reduce structural lipids and energy required for cell proliferation is an important reason for inhibiting tumor proliferation and causing tumor cell apoptosis. Therefore, the compound I-1 can inhibit the occurrence and development of tumors and has an important clinical application aspect.

Example 21

The effect of the compound shown as the formula I-1 on preadipocytes OP9 is detected:
(1) The cancer cells in the logarithmic growth phase are taken and inoculated into a 6 cm culture dish with the inoculation density of $2*10^6$ cells, and incubated under 5% $CO_2$ at 37° C.
(2) After cell adherence, 6 ml of 10% FBS culture medium containing 20 μM of the compound shown as the formula I is added into each dish with the culture medium as a negative control; cerulenin as a positive control; and 1 μM rosiglitazone (RSG) is used for differentiation.
(3) To observe the formation of lipid droplets, cells were incubated with 4% paraformaldehyde solution for 30 min at room temperature, washed with phosphate-buffered saline (PBS), and then stained with 0.5% oil red O in 60% isopropanol.
(4) After washing with distilled water, the stained cells were observed through a microscope, and then oil red O was extracted with isopropanol for quantification. This quantification was performed by measuring the absorbance of isopropanol solutions of oil red O at 510 nm.

Figure 6:
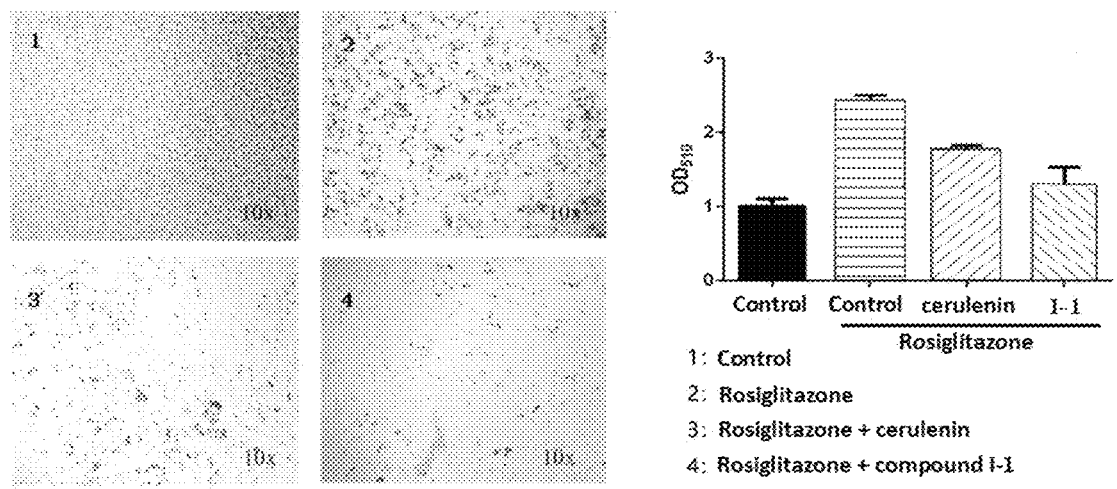
FIG. 6 shows the effect of a compound shown as a formula I on synthesis of lipid droplets in preadipocytes op9.

FIG. 6 shows the oil red staining condition of lipid droplets of cells op9 treated with the structural compound shown as the formula I under a microscope and the OD510 value measured after n-hexane dissolution. It can be seen from FIG. 6 that compared with the control group, the number of lipid droplets in cells OP9 treated with the structural compound shown as the formula I is reduced significantly, and the reduction magnitude is higher than that of an experimental group treated with cerulenin. The $OD_{510}$ value obtained in FIG. 6 also shows the same result, indicating that the structure shown as the formula I can inhibit the accumulation of lipid droplets in preadipocytes OP9.

Example 22

The effect of the structural compound shown as the formula I on the accumulation of lipid droplets in nematodes is detected:

Nematodes are taken and resuspended in an M9 buffer, 3 ml of nematode suspension is added into each test tube, the compound shown as the formula I is added into an experimental group to make the final concentration reach 10 μM, a group with no addition of the compound shown as the formula I is used as a control, the suspension is subjected to shaking culture on a shaker at 200 rpm/min, oil red staining is carried out after 9 days, the suspension is placed on a glass slide for observing the lipid droplet condition under a microscope.

Figure 7:
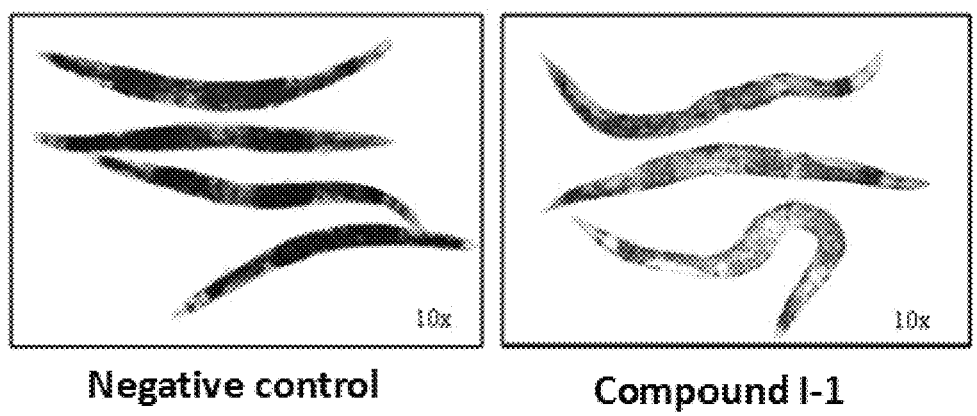
FIG. 7 shows the effect of a compound shown as a formula I on accumulation of nematode lipid droplets.

FIG. 7 shows the accumulation of lipid droplets in nematodes treated with the compound shown as the formula I for 9 days. As shown in the Figure, the color of the nematodes treated with the compound shown as the formula I is obviously lighter than the control group after oil red staining, obvious white areas can be seen, and nematodes of the control group appear dark as a whole without white areas. It can be seen that the accumulation of lipid droplets in nematodes treated with the compound shown as the formula I is significantly lower than that of the control group, indicating that the compound shown as the formula I can effectively inhibit the synthesis and accumulation of lipid droplets in nematodes. The inhibitory effect of the compound I-1 on the synthesis and accumulation of lipid droplets suggests that it can be effective in the treatment of metabolic diseases such as obesity.

Example 23

Figure 9:
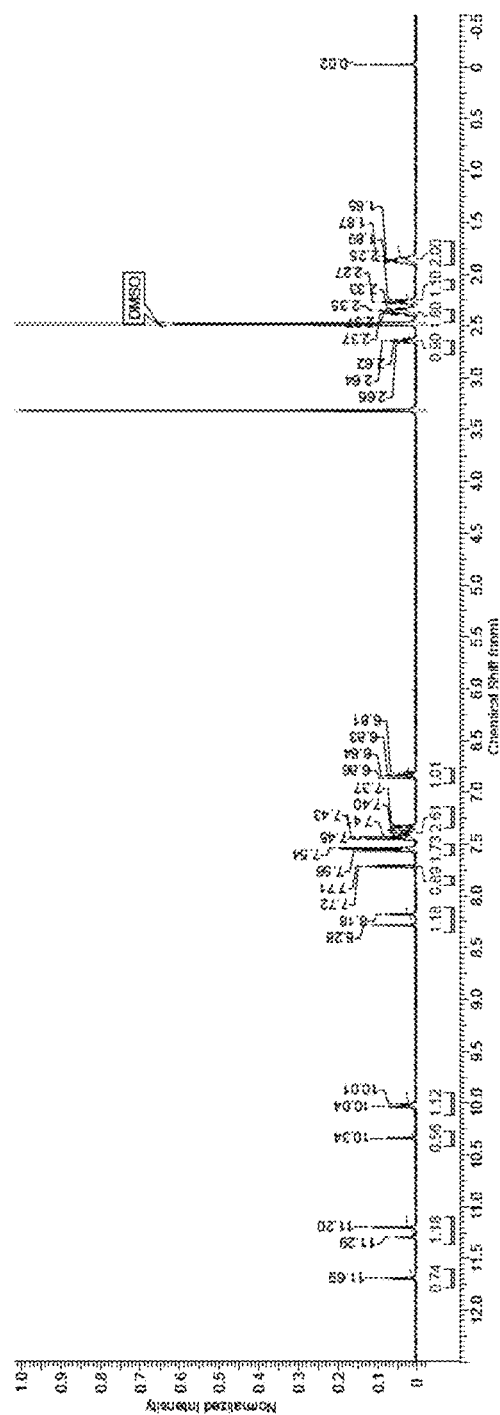
FIG. 9 is an NMR spectrum of a fatty acid synthase inhibitor shown as a formula I-1.

The effect of the compound shown as the formula I on the growth of transplanted tumors in mice:
(1) Cancer cells are cultured to a density of 80% (logarithmic growth phase), proceed according to a cell passage experiment, washed with PBS, subjected to digestion, centrifuged to remove the supernatant and then resuspended and washed twice in a serum-free culture medium; the concentration of a cell suspension is adjusted to be $2*10^2$ cells/ml with a serum-free culture medium; an equal volume of matrigel which has been melted overnight at 4° C. is added, shaken and mixed uniformly for use (all steps containing matrigel are operated on ice).
(2) 100 μl of cell and matrigel mixture is inoculated into the back of each nude mouse subcutaneously, after inoculation, the tumor growth condition is observed regularly every day to determine whether a transplanted tumor model is successful or not, and when the tumor volume is about 200 mm$^3$, drug treatment is started.
(3) In the experiment, nude mice (tumor formation rate 100%) with a successful transplanted tumor model are selected and adaptively fed for 7 days, a subcutaneous cancer cell transplantation experiment is carried out, after tumors are visible to the naked eyes, the nude mice is intraperitoneally injected with the compound I-1 every 2 days, the injection dosage is 5 mg/kg, an injection solvent group is used as a control, and each group have 5 mice. After 4 weeks of administration, tumors are taken and weighed (FIG. 9A).
(4) A tumor volume calculation formula:

$V=ab^2/2$, wherein $V$ is volume (mm$^3$), $a$ is length (mm), and $b$ is width (mm).

(5) After the tumors are sliced, H&E staining is carried out, and the changes in tumor tissues of the mice are observed.

Figure 8A:
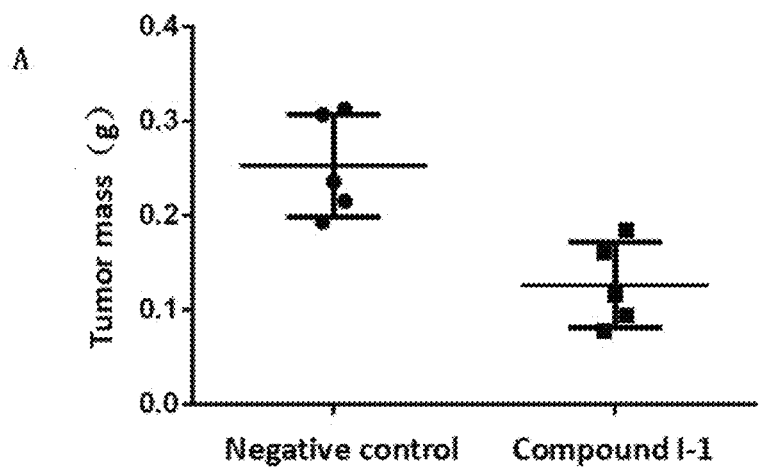
FIG. 8A shows the change in the tumor mass of mice after treatment with the compound I-1.
Figure 8B:
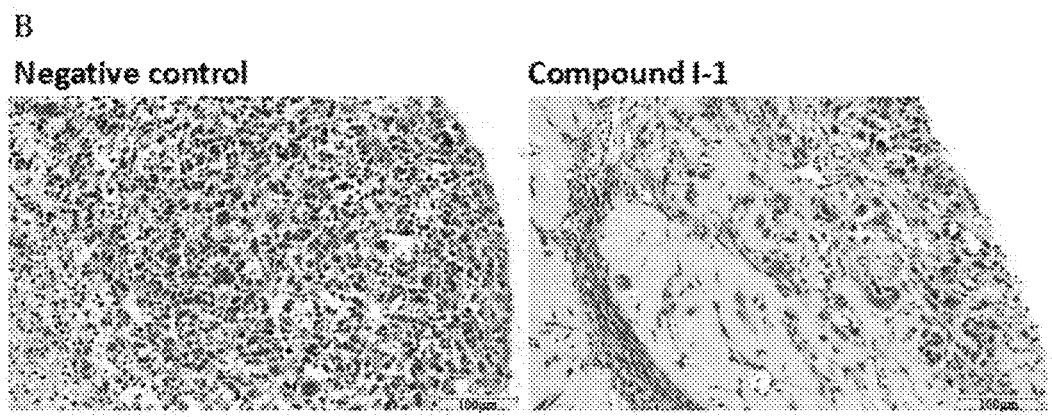
FIG. 8B shows the HE staining effect of transplanted tumors after treatment with the compound I-1.

FIG. 8A and FIG. 8B show the effect of the compound shown as the formula I-1 on transplanted tumors PC3 of mice. FIG. 8A shows the change in the tumor mass of mice after treatment with the compound I-1, and FIG. 8B shows the HE staining effect of transplanted tumors after treatment with the compound I-1. As shown in FIG. 8A, the tumor mass of mice treated with the compound shown as the formula I-1 for four weeks is significantly lower than that of the control group. FIG. 8B is a tumor HE stained slice. It can be observed that the mouse tumor tissues treated with the compound shown as the formula I have a large light color area, and a dark dotted area is significantly reduced, indicating that the compound shown as the formula I-1 can inhibit proliferation of tumors cells, resulting in large-area edema in the tumor tissues.

It can be seen from the above results that the compound I-1 has an obvious inhibitory effect on mouse tumors and the compound I-1 has an important application prospect as a new type of anti-tumor drug.

Example 24

The inhibitory effects of the compounds I-1 to I-8, the intermediate 1 and the intermediate 2 on the activity of FASN in HCT116 and the effect on the proliferation of tumor cells (PC-3 and HCT116) are detected.

The FASN enzyme activity measurement method shown in Experimental Example 18 is used to detect the effects of different substances on FASN enzyme activity. The method shown in Experimental Example 19 is used to detect the effects of different substances on the proliferation of tumor cells, cerulenin is used as a control, and the inhibition rates (%) of different substances on FASN enzyme activity and inhibition rates ($IC_{50}$ nM) on tumor proliferation are calculated. Detection results are shown as Table 1 below:

TABLE 1

The inhibitory effects of different substances on FASN enzyme activity and tumor proliferation

| | FASN enzyme activity inhibition rate (%) | PC-3 ($IC_{50}$ nM) | HCT116 ($IC_{50}$ nM) |
|---|---|---|---|
| Cerulenin | 21.32 | 18 ± 2.7 | 29 ± 3.2 |
| Compound I-1 | 58.63 | 9 ± 1.1 | 13 ± 1.7 |
| Compound I-2 | 30.73 | 16 ± 2.9 | 21 ± 1.6 |
| Compound I-3 | 41.22 | 14 ± 2.8 | 15 ± 2.5 |
| Compound I-4 | 49.02 | 11 ± 1.8 | 14 ± 1.7 |
| Compound I-5 | 39.17 | 15 ± 2.7 | 18 ± 2.9 |
| Compound I-6 | 41.87 | 15 ± 1.8 | 17 ± 2.7 |
| Compound I-7 | 37.67 | 15 ± 2.1 | 19 ± 1.9 |
| Compound I-8 | 35.22 | 16 ± 1.7 | 20 ± 3.5 |
| Intermediate 1 | 31.87 | 15 ± 1.3 | 19 ± 2.1 |
| Intermediate 2 | 22.16 | 18 ± 2.5 | 22 ± 3.1 |

It can be seen from the above Table 1 that the compounds I-1 to I-8 provided by the disclosure can effectively inhibit the activity of fatty acid synthase. The compound I-1 has the highest inhibition rate 58.63% on fatty acid synthase (FASN), which is significantly higher than the inhibition rate 21.32% of the positive control cerulenin. It can be seen that according to IC50 results, the effective concentration of the compound I-1 is also significantly lower than that of cerulenin, the mortality of prostate cancer cells PC3 can reach 50% when the effective concentration is 9+/−1.1 nM, and the mortality of colon cancer cells HCT116 can reach 50% when the effective concentration is 13+/−1.7 nM. Fatty acid synthase (FASN) participates in tumor fatty acid metabolism and cell cycle processes and plays an important role in tumor growth, invasion and migration. The compound with the structure shown as the general formula I-1 provided by the disclosure can be used as an FASN inhibitor, affect the synthesis and distribution of fatty acids in tumor cells, arrest the cell cycle in the interphase, prevent the mitosis of tumor cells and achieve inhibition of tumor proliferation. Therefore, as a new fatty acid synthase inhibitor, the compound with the structure shown as the general formula I has an important application prospect in the clinical treatment of tumors and the treatment of metabolic diseases such as obesity.

What is claimed is:

1. A method of use of a compound, comprising preparing medicines for inhibiting fatty acid synthase using the compound, wherein the structure of the compound is the general formula (I) or pharmaceutically acceptable salts thereof;

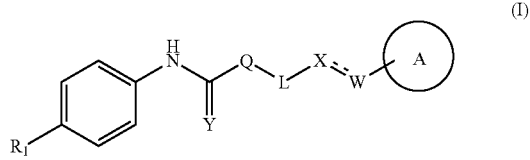

(I)

wherein, ----- is a single bond or a double bond; $R_1$ is independently selected from any one of hydroxyl, halogen, C1-C4 alkyl and C1-C4 alkoxy;
ring A is

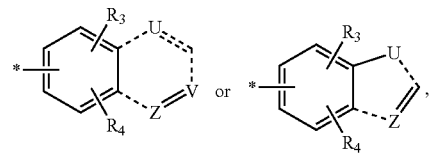

and U, V and Z are each independently selected from CH, N and NH; $R_3$ and $R_4$ are each independently selected from any one of hydrogen, halogen, hydroxyl, aryloxy and alkoxy, and $R_3$ and $R_4$ are not hydrogen at the same time;
Q is at least one heteroatom or $C_{1-5}$ straight or branched-chain hydrocarbyl containing no heteroatoms, and the heteroatoms are independently selected from nitrogen, oxygen and sulfur;
L is keto or imino;
W is selected from any one of —$(CH_2)_a$-, —$(CH_2)_a$—C(O)—, —$(CH_2)_a$—OC(O)— and —$(CH_2)_n$—C(O)O—,
wherein a is a natural number of 0-3; and
X is selected from —N(R)$_m$N(R)$_n$—, —C(O)N(R)$_n$— or —N(R)$_n$C(O)—, and m and n are each independently 0 or 1; R is independently hydrogen, halogen or phenyl; and Y is selected from nitrogen, oxygen or sulfur.

2. The method according to claim 1, wherein an aromatic ring of ring A in the general formula (I) is monocyclic aryl, naphthyl, [1,8]naphthyridinyl, benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolinyl, isoquinolinyl, oxazolo[5,4-b]pyridyl or oxazolo[5,4-c]pyridyl.

3. The method according to claim 1, wherein Q in the general formula (I) is selected from a $C_{1-5}$ straight or branched-chain hydrocarbyl with an end group of —N(R)—, —S—, —O—, —SO—, —SO2-, —NRC(O)—, —C(O)NR—, —N(R)SO2-, —SO2N(R)—, —OC(O)— or —C(O)O—.

4. The method according to claim 2, wherein Q in the general formula (I) is selected from a $C_{1-5}$ straight or branched-chain hydrocarbyl with an end group of —N(R)—, —S—, —O—, —SO—, —$SO_2$—, —NRC(O)—, —C(O)NR—, —N(R)$SO_2$—, —$SO_2$N(R)—, —OC(O)— or —C(O)O—.

5. The method according to claim 1, wherein the pharmaceutically acceptable salts of the compound shown as the general formula (I) comprises lactate, hydrochloride, phosphate, acetate, malate, citrate or aspartate.

6. The method according to claim 1, wherein W in the general formula (I) is —$CH_2$— or —C(O)—.

7. The method according to claim 1, wherein a dosage form of the medicines comprises decoction, pills, powder, ointments, pellets, medicinal liquor, syrup, extracts, lozenges, sticks, suppositories, herbal leavens, and moxa preparations; and the dosage form further comprises modern dosage forms of tablets, granules, bagged steeping drugs, oral liquids, capsules, dripping pills, mixtures, tinctures, aerosols, pellicle, powder injections and injections.

8. The method according to claim 5, wherein W in the general formula (I) is —$CH_2$— or —C(O)—.

9. A method for inhibiting expression of fatty acid synthase, comprising administering a pharmaceutical composition containing the compound shown as the general formula (I) or pharmaceutically acceptable salts thereof to a patient in need thereof.

10. The method according to claim 9, wherein the pharmaceutical composition further comprises other medically acceptable excipients, which comprises binders, fillers, disintegrants, lubricants, antioxidants, flavoring agents, aromatics, cosolvents, emulsifiers, solubilizers, osmotic pressure regulators and colorants.

11. The method according to claim 1, further comprising treating fatty acid metabolic diseases, cancer or immune diseases with the medicines.

12. The method according to claim 11, wherein a dosage form of the medicines comprises decoction, pills, powder, ointments, pellets, medicinal liquor, syrup, extracts, lozenges, sticks, suppositories, herbal leavens, and moxa preparations; and the dosage form further comprises modern dosage forms of tablets, granules, bagged steeping drugs, oral liquids, capsules, dripping pills, mixtures, tinctures, aerosols, pellicle, powder injections and injections.

13. The method according to claim 11, wherein the medicines further comprises other medically acceptable excipients, which comprises binders, fillers, disintegrants, lubricants, antioxidants, flavoring agents, aromatics, cosolvents, emulsifiers, solubilizers, osmotic pressure regulators and colorants.

* * * * *